US00RE39696E

(19) United States
(12) Reissued Patent
Cromlish et al.

(10) Patent Number: US RE39,696 E
(45) Date of Reissued Patent: Jun. 19, 2007

(54) HUMAN CYCLOOXYGENASE-2 CDNA AND ASSAYS FOR EVALUATING CYCLOOXYGENASE-2 ACTIVITY

(75) Inventors: Wanda A. Cromlish, Montreal (CA); Brian P. Kennedy, Kirkland (CA); Gary O'Neill, Dollard des Ormeaux (CA); Philip J. Vickers, Westborough, MA (US); Elizabeth Wong, St. Laurent (CA); Joseph A. Mancini, Kirkland (CA)

(73) Assignee: Merck Frosst Canada Ltd., Kirkland, Quebec (CA)

(21) Appl. No.: 09/731,632

(22) Filed: Nov. 20, 2000

Related U.S. Patent Documents

Reissue of:
(64) Patent No.: 5,543,297
Issued: Aug. 6, 1996
Appl. No.: 08/064,271
Filed: May 6, 1993

U.S. Applications:
(63) Continuation-in-part of application No. 07/994,760, filed on Dec. 22, 1992, now abandoned.

(51) Int. Cl.

| | |
|---|---|
| ***C12Q 1/26*** | (2006.01) |
| ***C12Q 1/00*** | (2006.01) |
| ***C12N 9/02*** | (2006.01) |
| ***C12N 5/06*** | (2006.01) |
| ***C07H 21/02*** | (2006.01) |
| | C12P 21/06 |

(52) U.S. Cl. ..... 435/25; 435/4; 435/6; 435/69.1; 435/183; 435/189; 435/252.3; 435/320.1; 435/325; 435/366; 435/240.2; 536/23.2; 536/23.5

(58) Field of Classification Search ..... 435/4, 435/6, 69.1, 183, 189, 252.3, 320.1, 325, 435/7.4; 536/23.2, 23.5, 23.7, 23.4
See application file for complete search history.

(56) References Cited

U.S. PATENT DOCUMENTS

| | | | |
|---|---|---|---|
| 4,562,155 | A | 12/1985 | Ricciardi et al. |
| 5,837,479 | A | 11/1998 | Young et al. |
| 6,048,850 | A | 4/2000 | Young et al. |

FOREIGN PATENT DOCUMENTS

| | | |
|---|---|---|
| JP | 63157980 | 6/1988 |
| JP | 1228479 | 9/1989 |
| WO | WO 94/06919 | 3/1994 |

OTHER PUBLICATIONS

Inflamm. Res. 46 (1997) 51–59, E. Wong, et al.
U.S. Appl. No. 07/949,780, Donald A. Young et al.
U.S. Appl. No. 08/054,364, Donald A. Young et al.
U.S. Appl. No. 07/983,835, Donald A. Young et al.
Jeanette A. M. Maier, et al., *The Journal of Biological Chemistry*, vol. 265, pp. 10805–10808 (1990).
Timothy Hla, et al., *The Journal of Biological Chemistry*, vol. 266, pp. 24059–24063 (1991).
Timothy Hla, et al., *Proc. Natl. Acad. Sci. USA,* vol. 89, pp. 7384–7388 (1992).
Funk, et al., *FASEB Jour.*, vol. 5, pp. 2304–2312 (1991).
Rodan, et al., *Journal of Bone and Mineral Research*, vol. 1, No. 2, pp. 213–220, (1986).
Patel, et al., *Virology*, vol. 149, No. 2, pp. 174–189 (1986).
Sato, et al., *Biochemical and Biophysical Research Communications*, vol. 141, No. 1, pp. 285–291 (1986).
Zhang, et al., *Prostaglandins Leukotriene and Essential Fatty Acids*, vol. 49, pp. 521–526 (1993).
O'Banion, et al., *Proc. Natl. Acad. Sci. USA*, vol. 89, pp. 4888–4892 (1992).
Wiesenberg–Boettcher, et al., *Drugs Exptl. Clin. Res.*, XV (11/12), pp. 501–509 (1989).
Tsuji, et al., *Chem. Pharm. Bull.*, vol. 40, No. 9, pp. 2399–2409 (1992).
Gans, et al., *The Journal of Pharmacology and Experimental Therapeutics*, vol. 254, No. 1, pp. 180–187 (1990).
Hoff, et al., *Federation of European Biochemical Societies*, vol. 320, No. 1, pp. 38–42 (1993).
ACS 1994 Registry No. 80937–31–1, Flosulide.
David A. Jones, et al., *The Journal of Biological Chemistry*, vol. 268, No. 12, pp. 9049–9054 (1993).
P. Ryseck, et al., *Cell Growth & Differentiation*, vol. 3, pp. 443–450 (1992).
Timothy Hla, et al., *Proc. Natl. Acad. Sci. USA*, vol. 89, pp. 7384–7388 (1992).
Weilin Xie, et al., *Drug Development Research*, vol. 25, pp. 249–265 (1992).
Jean Sirois, et al., *The Journal of Biological Chemistry*, vol. 267, No. 9, pp. 6382–6388 (1992).
Bradley S. Fletcher, et al., *The Journal of Biological Chemistry*, vol. 267, No. 7, pp. 4338–4344 (1992).
M. Kerry O'Banion, et al., *The Journal of Biological Chemistry*, vol. 266, No. 34, pp. 23261–23267 (1991).
Dean A. Kujubu, et al., *The Journal of Biological Chemistry*, vol. 266, No. 20, pp. 12866–12872 (1991).
Daniel L. Simmons, et al., *Prostaglandins, Leukotrienes, Lipoxins, and PAF*, pp. 67–78 (1991).
Weilin Xie, et al., *Proc. Natl. Acad. Sci. USA*, vol. 88, pp. 2692–2696 (1991).
Glenn D. Rosen, et al., *Biochemical and Biophysical Research Communications*, vol. 164, No. 3, pp. 1358–1365 (1989).
David L. DeWitt, et al., *Proc. Natl. Acad. Sci. USA*, vol. 85, pp. 1412–1416 (1988).
Chieko Yokoyama, et al., *Federation of European Biochemical Societies*, vol. 231, No. 2, pp. 347–351 (1988).
John P. Merlie, et al., *The Journal of Biological Chemistry*, vol. 263, No. 8, pp. 3550–3553 (1988).

*Primary Examiner*—Manjunath N. Rao
(74) *Attorney, Agent, or Firm*—Curtis C. Panzer; David L. Rose

(57) ABSTRACT

The invention discloses a human cyclooxygenase-2 cDNA, a human cyclooxygenase-2 and assays for preferentially and independently measuring cyclogenase-2 or cyclooxygenase-1 activity present in a given sample.

19 Claims, 4 Drawing Sheets

FIG. 1A

Met Leu Ala Arg Ala Leu Leu Leu Cys Ala Val Leu Ala Leu Ser His
1 5 10 15

Thr Ala Asn Pro Cys Cys Ser His Pro Cys Gln Asn Arg Gly Val Cys
20 25 30

Met Ser Val Gly Phe Asp Gln Tyr Lys Cys Asp Cys Thr Arg Thr Gly
35 40 45

Phe Tyr Gly Glu Asn Cys Ser Thr Pro Glu Phe Leu Thr Arg Ile Lys
50 55 60

Leu Phe Leu Lys Pro Thr Pro Asn Thr Val His Tyr Ile Leu Thr His
65 70 75 80

Phe Lys Gly Phe Trp Asn Val Val Asn Asn Ile Pro Phe Leu Arg Asn
85 90 95

Ala Ile Met Ser Tyr Val Leu Thr Ser Arg Ser His Leu Ile Asp Ser
100 105 110

Pro Pro Thr Tyr Asn Ala Asp Tyr Gly Tyr Lys Ser Trp Glu Ala Phe
115 120 125

Ser Asn Leu Ser Tyr Tyr Thr Arg Ala Leu Pro Pro Val Pro Asp Asp
130 135 140

Cys Pro Thr Pro Leu Gly Val Lys Gly Lys Lys Gln Leu Pro Asp Ser
145 150 155 160

Asn Glu Ile Val Glu Lys Leu Leu Leu Arg Arg Lys Phe Ile Pro Asp
165 170 175

Pro Gln Gly Ser Asn Met Met Phe Ala Phe Phe Ala Gln His Phe Thr
180 185 190

His Gln Phe Phe Lys Thr Asp His Lys Arg Gly Pro Ala Phe Thr Asn
195 200 205

Gly Leu Gly His Gly Val Asp Leu Asn His Ile Tyr Gly Glu Thr Leu
210 215 220

Ala Arg Gln Arg Lys Leu Arg Leu Phe Lys Asp Gly Lys Met Lys Tyr
225 230 235 240

Gln Ile Ile Asp Gly Glu Met Tyr Pro Pro Thr Val Lys Asp Thr Gln
245 250 255

Ala Glu Met Ile Tyr Pro Pro Gln Val Pro Glu His Leu Arg Phe Ala
260 265 270

Val Gly Gln Glu Val Phe Gly Leu Val Pro Gly Leu Met Met Tyr Ala
275 280 285

Thr Ile Trp Leu Arg Glu His Asn Arg Val Cys Asp Val Leu Lys Gln
290 295 300

FIG 1B

Glu His Pro Glu Trp Gly Asp Glu Gln Leu Phe Gln Thr Ser Arg Leu
305 310 315 320

Ile Leu Ile Gly Glu Thr Ile Lys Ile Val Ile Glu Asp Tyr Val Gln
325 330 335

His Leu Ser Gly Tyr His Phe Lys Leu Lys Phe Asp Pro Glu Leu Leu
340 345 350

Phe Asn Lys Gln Phe Gln Tyr Gln Asn Arg Ile Ala Ala Glu Phe Asn
355 360 365

Thr Leu Tyr His Trp His Pro Leu Leu Pro Asp Thr Phe Gln Ile His
370 375 380

Asp Gln Lys Tyr Asn Tyr Gln Gln Phe Ile Tyr Asn Asn Ser Ile Leu
385 390 395 400

Leu Glu His Gly Ile Thr Gln Phe Val Glu Ser Phe Thr Arg Gln Ile
405 410 415

Ala Gly Arg Val Ala Gly Gly Arg Asn Val Pro Pro Ala Val Gln Lys
420 425 430

Val Ser Gln Ala Ser Ile Asp Gln Ser Arg Gln Met Lys Tyr Gln Ser
435 440 445

Phe Asn Glu Tyr Arg Lys Arg Phe Met Leu Lys Pro Tyr Glu Ser Phe
450 455 460

Glu Glu Leu Thr Gly Glu Lys Glu Met Ser Ala Glu Leu Glu Ala Leu
465 470 475 480

Tyr Gly Asp Ile Asp Ala Val Glu Leu Tyr Pro Ala Leu Leu Val Glu
485 490 495

Lys Pro Arg Pro Asp Ala Ile Phe Gly Glu Thr Met Val Glu Val Gly
500 505 510

Ala Pro Phe Ser Leu Lys Gly Leu Met Gly Asn Val Ile Cys Ser Pro
515 520 525

Ala Tyr Trp Lys Pro Ser Thr Phe Gly Gly Glu Val Gly Phe Gln Ile
530 535 540

Ile Asn Thr Ala Ser Ile Gln Ser Leu Ile Cys Asn Asn Val Lys Gly
545 550 555 560

Cys Pro Phe Thr Ser Phe Ser Val Pro Asp Pro Glu Leu Ile Lys Thr
565 570 575

Val Thr Ile Asn Ala Ser Ser Ser Arg Ser Gly Leu Asp Asp Ile Asn
580 585 590

Pro Thr Val Leu Leu Lys Glu Arg Ser Thr Glu Leu (SEQ ID NO: 10)
595 600

FIG. 2A

GTCCAGGAAC TCCTCAGCAG CGCCTCCTTC AGCTCCACAG CCAGACGCCC TCAGACAGCA 60
AAGCCTACCC CCGCGCCGCG CCCTGCCCGC CGCTGCGATG CTCGCCCCGCG CCCTGCTGCT 120
GTGCCGCGTC CTGGCGCTCA GCCATACAGC AAATCCTTGC TGTTCCCACC CATGTCAAAA 180
CCGAGGTGTA TGTATGAGTG TGGGATTTGA CCAGTATAAG TGCGATTGTA CCCGGACAGG 240
ATTCTATGGA GAAAACTGCT CAACACCGGA ATTTTTGACA AGAATAAAAT TATTTCTGAA 300
ACCCACTCCA AACACAGTGC ACTACATACT TACCCACTTC AAGGGATTTT GGAACGTTGT 360
GAATAACATT CCCTTCCTTC GAAATGCAAT TATGAGTTAT GTGTTGACAT CCAGATCACA 420
TTTGATTGAC AGTCCACCAA CTTACAATGC TGACTATGGC TACAAAAGCT GGGAAGCCTT 480
CTCTAACCTC TCCTATTATA CTAGAGCCCT TCCTCCTGTG CCTGATGATT GCCCGACTCC 540
CTTGGGTGTC AAAGGTAAAA AGCAGCTTCC TGATTCAAAT GAGATTGTGG AAAAATTGCT 600
TCTAAGAAGA AAGTTCATCC CTGATCCCCA GGGCTCAAAC ATGATGTTTG CATTCTTTGC 660
CCAGCACTTC ACGCACCAGT TTTTCAAGAC AGATCATAAG CGAGGGCCAG CTTTCACCAA 720
CGGGCTGGGC CATGGGGTGG ACTTAAATCA TATTTACGGT GAAACTCTGG CTAGACAGCG 780
TAAACTGCGC CTTTTCAAGG ATGGAAAAAT GAAATATCAG ATAATTGATG GAGAGATGTA 840
TCCTCCCACA GTCAAAGATA CTCAGGCAGA GATGATCTAC CCTCCTCAAG TCCCTGAGCA 900
TCTACGGTTT GCTGTGGGGC AGGAGGTCTT TGGTCTGGTG CCTGGTCTGA TGATGTATGC 960
CACAATCTGG CTGCGGGAAC ACAACAGAGT ATGTGATGTG CTTAAACAGG AGCATCCTGA 1020
ATGGGGTGAT GAGCAGTTGT TCCAGACAAG CAGGCTAATA CTGATAGGAG AGACTATTAA 1080
GATTGTGATT GAAGATTATG TGCAACACTT GAGTGGCTAT CACTTCAAAC TGAAATTTGA 1140
CCCAGAACTA CTTTTCAACA AACAATTCCA GTACCAAAAT CGTATTGCTG CTGAATTTAA 1200
CACCCTCTAT CACTGGCATC CCCTTCTGCC TGACACCTTT CAAATTCATG ACCAGAAATA 1260
CAACTATCAA CAGTTTATCT ACAACAACTC TATATTGCTG GAACATGGAA TTACCCAGTT 1320
TGTTGAATCA TTCACCAGGC AAATTGCTGG CAGGGTTGCT GGTGGTAGGA ATGTTCCACC 1380
CGCAGTACAG AAAGTATCAC AGGCTTCCAT TGACCAGAGC AGGCAGATGA AATACCAGTC 1440
TTTTAATGAG TACCGCAAAC GCTTTATGCT GAAGCCCTAT GAATCATTTG AAGAACTTAC 1500
AGGAGAAAAG GAAATGTCTG CAGAGTTGGA AGCACTCTAT GGTGACATCG ATGCTGTGGA 1560
GCTGTATCCT GCCCTTCTGG TAGAAAAGCC TCGGCCAGAT GCCATCTTTG GTGAAACCAT 1620
GGTAGAAGTT GGAGCACCAT TCTCCTTGAA AGGACTTATG GGTAATGTTA TATGTTCTCC 1680
TGCCTACTGG AAGCCAAGCA CTTTTGGTGG AGAAGTGGGT TTTCAAATCA TCAACACTGC 1740

FIG. 2B

```
CTCAATTCAG TCTCTCATCT GCAATAACGT GAAGGGCTGT CCCTTTACTT CATTCAGTGT 1800
TCCAGATCCA GAGCTCATTA AAACAGTCAC CATCAATGCA AGTTCTTCCC GCTCCGGACT 1860
AGATGATATC AATCCCACAG TACTACTAAA AGAACGGTCG ACTGAACTGT AGAAGTCTAA 1920
TGATCATATT TATTTATTTA TATGAACCAT GTCTATTAAT TTAATTATTT AATAATATTT 1980
ATATTAAACT CCTTATGTTA CTTAACATCT TCTGTAACAG AAGTCAGTAC TCCTGTTGCG 2040
GAGAAAGGAG TCATACTTGT GAAGACTTTT ATGTCACTAC TCTAAAGATT TTGCTGTTGC 2100
TGTTAAGTTT GGAAAACAGT TTTTATTCTG TTTTATAAAC CAGAGAGAAA TGAGTTTTGA 2160
CGTCTTTTTA CTTGAATTTC AACTTATATT ATAAGGACGA AAGTAAAGAT GTTTGAATAC 2220
TTAAACACTA TCACAAGATG CCAAAATGCT GAAAGTTTTT ACACTGTCGA TGTTTCCAAT 2280
GCATCTTCCA TGATGCATTA GAAGTAACTA ATGTTTGAAA TTTTAAAGTA CTTTTGGGTA 2340
TTTTTCTGTC ATCAAACAAA ACAGGTATCA GTGCATTATT AAATGAATAT TTAAATTAGA 2400
CATTACCAGT AATTTCATGT CTACTTTTTA AAATCAGCAA TGAAACAATA ATTTGAAATT 2460
TCTAAATTCA TAGGGTAGAA TCACCTGTAA AAGCTTGTTT GATTTCTTAA AGTTATTAAA 2520
CTTGTACATA TACCAAAAAG AAGCTGTCTT GGATTTAAAT CTGTAAAATC AGATGAAATT 2580
TTACTACAAT TGCTTGTTAA AATATTTTAT AAGTGATGTT CCTTTTTCAC CAAGAGTATA 2640
AACCTTTTTA GTGTGACTGT TAAAACTTCC TTTTAAATCA AAATGCCAAA TTTATTAAGG 2700
TGGTGGAGCC ACTGCAGTGT TATCTCAAAA TAAGAATATC CTGTTGAGAT ATTCCAGAAT 2760
CTGTTTATAT GGCTGGTAAC ATGTAAAAAC CCCATAACCC CGCCAAAAGG GGTCCTACCC 2820
TTGAACATAA AGCAATAACC AAAGGAGAAA AGCCCAAATT ATTGGTTCCA AATTTAGGGT 2880
TTAAACTTTT TGAAGCAAAC TTTTTTTTAG CCTTGTGCAC TGCAGACCTG GTACTCAGAT 2940
TTTGCTATGA GGTTAATGAA GTACCAAGCT GTGCTTGAAT AACGATATGT TTTCTCAGAT 3000
TTTCTGTTGT ACAGTTTAAT TTAGCAGTCC ATATCACATT GCAAAAGTAG CAATGACCTC 3060
ATAAAATACC TCTTCAAAAT GCTTAAATTC ATTTCACACA TTAATTTTAT CTCAGTCTTG 3120
AAGCCAATTC AGTAGGTGCA TTGGAATCAA GCCTGGCTAC CTGCATGCTG TTCCTTTTCT 3180
TTTCTTCTTT TAGCCATTTT GCTAAGAGAC ACAGTCTTCT CAAACACTTC GTTTCTCCTA 3240
TTTTGTTTTA CTAGTTTTAA GATCAGAGTT CACTTTCTTT GGACTCTGCC TATATTTTCT 3300
TACCTGAACT TTTGCAAGTT TTCAGGTAAA CCTCAGCTCA GGACTGCTAT TTAGCTCCTC 3360
TTAAGAAGAT TAAAAAAAAA AAAAAAG (SEQ ID NO: 11)                     3387
```

HUMAN CYCLOOXYGENASE-2 CDNA AND ASSAYS FOR EVALUATING CYCLOOXYGENASE-2 ACTIVITY

Matter enclosed in heavy brackets [ ] appears in the original patent but forms no part of this reissue specification; matter printed in italics indicates the additions made by reissue.

RELATED U.S. APPLICATION DATA

This application is a Continuation-in-Part of U.S. Ser. No. 07/994,760, filed Dec. 22, 1992, now abandoned.

BACKGROUND OF THE INVENTION

This invention relates to human cyclooxygenase-2 cDNA and assays for evaluation cyclooxygenase-1 and cyclooxygenase-2 activity.

Non-steroidal, antiinflammatory drugs exert most of their antiinflammatory, analgesic and antipyretic activity and inhibit hormone-induced uterine contractions and certain types of cancer growth through inhibition of prostaglandin G/H synthase, also known as cyclooxygenase. Up until recently, only one form of cyclooxygenase had been characterized, this corresponding to cyclooxygenase-1 or the constitutive enzyme, as originally identified in bovine seminal vesicles. Recently the gene for an inducible form of cyclooxygenase (cyclooxygenase-2) has been cloned, sequenced and characterized from chicken, murine and human sources. This enzyme is distinct from the cyclooxygenase-1 which has also been cloned, sequenced and characterized from sheep, murine and human sources. The second form of cyclooxygenase, cyclooxygenase-2, is rapidly and readily inducible by a number of agents including mitogens, endotoxin, hormones, cytokines and growth factors. As prostaglandins have physiological and pathological roles, we have concluded that the constitutive enzyme, cyclooxygenase-1, is responsible, in large part, for endogenous basal release of prostaglandins and hence is important in their physiological functions such as the maintenance of gastrointestinal integrity and renal blood flow. In contrast, we have concluded that the inducible form, cyclooxygenase-2, is mainly responsible for the pathological effects of prostaglandins where rapid induction of the enzyme would occur in response to such agents as inflammatory agents, hormones, growth factors, and cytokines. Thus, a selective inhibitor of cyclooxygenase-2 will have similar antiinflammatory, antipyretic and analgesic properties of a conventional non-steroidal antiinflammatory drug (NSAID), and in addition would inhibit hormone-induced uterine contractions and have potential anti-cancer effects, but will have a diminished ability to induce some of the mechanism-based side effects. In particular, such a compound should have a reduced potential for gastrointestinal toxicity, a reduced potential for renal side effects, a reduced effect on bleeding times and possibly a lessened ability to induce asthma attacks in aspirin-sensitive asthmatic subjects.

Accordingly, it is an object of this invention to provide assays and materials to identify and evaluate pharmacological agents that are potent inhibitors of cyclooxygenase-2 and cyclooxygenase-2 activity.

It is also an object of this invention to provide assays and materials to identify and evaluate pharmacological agents that preferentially or selectively inhibit cyclooxygenase 2 and cyclooxygenase 2 activity over cyclooxygenase 1 and cyclooxygenase 1 activity.

BRIEF DESCRIPTION OF THE DRAWINGS

FIG. 1 Full length amino acid sequence of a human cyclooxygenase-2 protein.

FIG. 2 Full length nucleotide sequence of a cloned human cyclooxygenase-2 complementary DNA obtained from human osteosarcoma cells.

SUMMARY OF THE INVENTION

The invention encompasses a human osteosarcoma cell cyclooxygenase-2 cDNA and a human cyclooxygenase-2 protein.

The invention also encompasses assays to identify and evaluate pharmacological agents that are potent inhibitors of cyclooxygenase 2 and cyclooxygenase 2 activity. The invention also encompasses assays to identify and evaluate pharmacological agents that preferentially or selectively inhibit cyclooxygenase-2 and cyclooxygenase-2 activity over cyclooxygenase-1.

DETAILED DESCRIPTION OF THE INVENTION

In one embodiment the invention encompasses an assay for determining the cyclooxygenase-2 activity of a sample comprising the steps of:

(a) adding
  (1) a human osteosarcoma cell preparation,
  (2) a sample, said sample comprising a putative cyclooxygenase-2 inhibitor, and
  (3) arachidonic acid; and (b) determining the amount of prostaglandin $E_2$ produced in step (a).

For purposes of this specification human osteosarcoma cells are intended to include, but are not limited to human osteosarcoma cell lines available from ATCC [Rockville, Md.] *P.O. Box 1549, Manassas, Va. 20108* such as osteosarcoma 143B is (ATCC CRL 8303) and osteosarcoma 143B PML BK TK (ATCC CRL 8304. We have found useful, osteosarcoma 143.98.2 which was originally obtained from Dr. William Sugden, McArdle Laboratory for Cancer Research, University of Wisconsin-Madison. We have now made a Budapest Treaty deposit of osteosarcoma 143.98.2 with ATCC on Dec. 22, 1992 under the identification Human osteosarcoma 143.98.2 (now ATCC CRL 11226).

For purposes of this specification the osteosarcoma cell preparation shall be defined as an aqueous mono layer or suspension of human osteosarcoma cells, a portion of which will catalyze the synthesis of PGE2. Furthermore the preparation contains a buffer such as HANK'S balanced salt solution.

Within this embodiment is the genus where the human osteosarcoma cells are from the osteosarcoma 143 family of TK; we have used osteosarcoma 143.98.2.

For purposes of this specification the osteosarcoma cell preparation also includes human osteosarcoma microsomes, said a portion of which will catalyze the synthesis of $PGE_2$. The microsomes may be obtained as described below from any of the osteosarcoma cell lines herein disclosed.

In a second embodiment the invention encompasses a composition comprising (a) an osteosarcoma cell preparation, having $10^3$ to $10^9$ osteosarcoma cells per cc of cell preparation, and (b) 0.1 to 50 μl of peroxide-free arachidonic acid per cc of cell preparation.

Typically the cell preparation will be grown as a monolayer ann used in an aliquot of $8.2\times10^4$ to $2\times10^6$ cells per well (of approximately 1 cc working volume) as described in the protocol below. Arachidonic acid is typically used in amounts of 1 to 20 ul per well of approximately 1 cc working volume.

When osteosarcoma microsomes are used instead of whole cells, the cell preparation will typically comprise 50 to 500 ug of microsomal protein per cc of cell preparation. Arachidonic acid is typically used in amounts of 1 to 20 μl acid per cc of cell preparation.

In a third embodiment the invention encompasses an assay for determining the cyclooxygenase-1 activity of a sample comprising the steps of:

(a) adding (1) a cell preparation, said cells capable of expressing cyclooxygenase-1, but not expressing cyclooxygenase-2, (2) a sample, said sample comprising a putative cyclooxygenase-1 inhibitor;

(3) arachidonic acid; and (b) determining the amount of prostaglandin $E_2$ produced in step (a).

For purposes of this specification cells capable of expressing cyclooxygenase-1 but incapable of expressing cyclooxygenase-2, includes the human histiocytic lymphoma cells such as U-937 (ATCC CRL 1593). Such cells are hereinafter described as COX-1 cells.

For purposes of this specification the cell preparation shall be defined as an aqueous suspension of cell, typically at a concentration of $8\times10^5$ to $1\times10^7$ cells/ml. The suspension will contain a buffer as defined above.

In a fourth embodiment the invention encompasses a human cyclooxygenase-2 which is shown in FIG. 1. This Cyclooxygenase-2 is also identified as SEQ. ID. NO:10:.

In a fifth embodiment the invention encompasses a human Cyclooxygenase-2 cDNA which is shown in FIG. 2 or a degenerate variation thereof. This Cyclooxygenase-2 cDNA is also identified as SEQ. ID. NO:11:.

Within this embodiment is the reading frame portion of the sequence shown in FIG. 2 encoding the cyclooxygenase-2 shown in FIG. 1; said portion being bases 97 through 1909.

As will be appreciated by those of skill in the art, there is a substantial amount of redundency in the set of codons which translate specific amino acids. Accordingly, the invention also includes alternative base sequences wherein a codon (or codons) are replaced with another codon, such that the amino acid sequence translated by the DNA sequence remains unchanged. For purposes of this specification, a sequence bearing one or more such replaced codons will be defined as a degenerate variation. Also included are mutations (exchange of individual amino acids) which produce no significant effect in the expressed protein.

In a sixth embodiment the invention encompasses a system for stable expression of cyclooxygenase-2 as shown in FIG. 2 or a degenerate variation thereof comprising:

(a) an expression vector such as vacinia expression vector pTM1, baculovirus expression vector pJVETLZ, pUL941 and pAcmP1 INVITROGEN vectors pCEP4 and pcDNAI; and (b) a base sequence encoding human cyclooxygenase-2 as shown in FIG. 2 or a degenerate variation thereof.

In one genus of this embodiment cyclooxygenase-2 is expressed in Sf9 or Sf21 cells (INVITROGEN).

A variety of mammalian expression vectors may be used to express recombinant cyclooxygenase-2 in mammalian cells. Commercially available mammalian expression vectors which may be suitable for recombinant cyclooxygenase-2 expression, include but are not limited to, pMC1 neo (Stratagene), pXT1 (Stratagene), pSG5 (Stratagene), EBO-pSV2-neo (ATCC 37593) pBPV-1(8-2) (ATCC 37110), pdBPV-MMTneo(342-12) (ATCC 37224), pRSVgpt (ATCC 37199), pRSVneo (ATCC 37198), pSV2-dhfr (ATCC 37146), pUCTag (ATCC 37460), and gZD35 (ATCC 37565).

DNA encoding cyclooxygenase-2 may also be cloned into an expression vector for expression in a recombinant host cell. Recombinant host cells may be prokaryotic or eukaryotic, including but not limited to bacteria, yeast, mammalian cells including but not limited to cell lines of human, bovine, porcine, monkey and rodent origin, and insect cells including but not limited to drosophila derived cell lines. Cell lines derived from mammalian species which may be suitable and which are commercially available, include but are not limited to, CV-1 (ATCC CCL 70), COS-1 (ATCC CRL 1650), COS-7 (ATCC CRL 1651), CHO-K1 (ATCC CCL 61), 3T3 (ATCC CCL 92), NIH/3T3 (ATCC CRL 1658), HeLa (ATCC CCL 2), C127I (ATCC CRL 1616), BS-C-1 (ATCC CCL 26) and MRC-5 (ATCC CCL 171).

The expression vector may be introduced into host cells via any one of a number of techniques including but not limited to transformation, transfection, protoplast fusion, and electroporation. The expression vector-containing cells are clonally propagated and individually analyzed to determine whether they produce cyclooxygenase-2 protein. Identification of cyclooxygenase-2 expressing host cell clones may be done by several means, including but not limited to immunological reactivity with anti-cyclooxygenase-2 antibodies, and the presence of host cell-associated cyclooxygenase-2 activity.

Expression of cyclooxygenase-2 DNA may also be performed using in vitro produced synthetic mRNA. Synthetic mRNA can be efficiently translated in various cell-free systems, including but not limited to wheat germ extracts and reticulocyte extracts, as well as efficiently translated in cell based systems, including but not limited to microinjection into frog oocytes, with microinjection into frog oocytes being preferred.

To determine the cyclooxygenase-2 cDNA sequence(s) that yields optimal levels of enzymatic activity and/or cyclooxygenase-2 protein, cyclooxygenase-2 cDNA molecules including but not limited to the following can be constructed: the full-length open reading frame of the cyclooxygenase-2 cDNA (base 97 to base 1909). All constructs can be designed to contain none, all or portions of the 3' untranslated region of cyclooxygenase-2 cDNA (base 1910-3387).

Cyclooxygenase-2 activity and levels of protein expression can be determined following the introduction, both singly and in combination, of these constructs into appropriate host cells. Following determination of the cyclooxygenase-2 cDNA cassette yielding optimal expression in transient assays, this cyclooxygenase-2 cDNA construct is transferred to a variety of expression vectors, including but not limited to mammalian cells, baculovirus-infected insect cells, *E. Coli,* and the yeast S. cerevisiae.

Mammalian cell transfectants, insect cells and microinjected oocytes are assayed for both the levels of cyclooxygenase-2 enzymatic activity and levels of cyclooxygenase-2 protein by the following methods. The first method for assessing cyclooxygenase-2 enzymatic activity involves the incubation of the cells in the presence of 20 μM arachidonic acid for 10 minutes and measuring the $PGE_2$ production by EIA.

The second method for detecting cyclooxygenase-2 activity involves the direct measurement of cyclooxygenase-2 activity in cellular lysates or microsomes prepared from mammalian cells transfected with cyclooxygenase-2 cDNA or oocytes injected with cyclooxygenase-2 mRNA. This assay can be performed by adding arachidonic acid to lysates and measuring the PGE2 production by EIA.

Levels of cyclooxygenase-2 protein in host cells is quantitated by immunoaffinity and/or ligand affinity techniques. cyclooxygenase-2 specific affinity beads or cyclooxygenase-2 specific antibodies are used to isolate $^{35}$S-methionine labelled or unlabelled cyclooxygenase-2 protein. Labelled cyclooxygenase-2 protein is analyzed by SDS-PAGE. Unlabelled cyclooxygenase-2 protein is detected by Western blotting, ELISA or RIA assays employing cyclooxygenase-2 specific antibodies.

Following expression of cyclooxygenase-2 in a recombinant host cell, cyclooxygenase-2 protein may be recovered to provide cyclooxygenase-2 in active form, capable of participating in the production of $PGE_2$. Several cyclooxygenase-2 purification procedures are available and suitable for use. As described above for purification of cyclooxygenase-2 from natural sources, recombinant cyclooxygenase-2 may be purified from cell lysates and extracts, by various combinations of, or individual application of salt fractionation, ion exchange chromatography, size exclusion chromatography, hydroxylapatite adsorption chromatography and hydrophobic interaction chromatography.

In addition, recombinant cyclooxygenase-2 can be separated from other cellular proteins by use of an immunoaffinity column made with monoclonal or polyclonal antibodies specific for full length nascent cyclooxygenase-2.

THE WHOLE CELL ASSAYS

For the cyclooxygenase-2 and cyclooxygenase-1 assays, human osteosarcoma cells were cultured and used in aliquots of typical $8\times10^4$ to $2\times10^6$ cells/well. We have found it convenient to culture the cells in 1 ml of media in 24-well multidishes (NUNCLON) until essentially confluent. The number of cells per assay may be determined from replicate plates prior to assays, using standard procedures. Prior to the assay, the cells are washed with a suitable buffer such as Hanks balanced salts solution (HBSS; SIGMA), preferably prewarmed to 37° C. Approximately 0.5 to 2 ml is then added per well.

Prior to the assays, the appropriate number of COX-1 cells ($10^5$ to $10^7$ cells/ml) are removed from cultures and concentrated such as by centrifugation at 300×g for 10 minutes. The supernatant is decanted and cells washed, in a suitable buffer. Preferably, cells are again concentrated, such as by centrifugation at 300×g for 10 minutes and resuspended to a final cell density of approximately $1.5\times10^6$, cells/ml, preferably in prewarmed HBSS.

Following incubation of human osteosarcoma cells or COX-1 cells in a suitable buffer, test compound and/or vehicle samples (such as DMSO) are added, and the resulting composition gently mixed. Preferably the assay is performed in triplicate. The arachidonic acid is then added in proportions as described above. We prefer to incubate the cells for approximately 5 minutes at 30° to 40° C., prior to the addition of the of peroxide-free arachidonic acid (CAYMAN) diluted in a suitable buffer such as HBSS. Control samples should contain ethanol or other vehicle instead of arachidonic acid. A total reaction incubation time of 5 to 10 minutes at to 37° C. has proven satisfactory. For osteosarcoma cells, reactions may be stopped by the addition HCl or other acid, preferably combined with mixing, or rapid removal of media directly from cell monolayers. For U-937 cells, reaction may be advantageously be performed in multiwell dishes or microcentrifuge tubes and stopped by the addition of HCl or other mineral acid. Typically, samples assayed in 24-multidishes are then transferred to microcentrifuge tubes, and all samples frozen on dry ice. Similarly, samples are typically stored at −20° C. or below prior to analysis of $PGE_2$ levels.

Quantitation of $PGE_2$ concentrations

Stored osteosarcoma 143 and U-937 samples are thawed, if frozen, and neutralized, if stored in acid. Samples are then preferably mixed, such as by vortexing, and $PGE_2$ levels measured using a $PGE_2$ enzyme immunoassay, such as is commercially available from CAYMAN. We have advantageously conducted the plating, washing and colour development steps as an automated sequence using a BIOMEK 1000 (BECKMAN). In our preferred procedure, following the addition of ELLMANS reagent, color development is monitored at 415 nm using the BIORAD model 3550 microplate reader with MICROPLATE MANAGER/PC DATA ANALYSIS software. Levels of $PGE_2$ are calculated from the standard curve, and may optionally determined using BECKMAN IMMUNOFIT EIA/RIA analysis software.

In the absence of the addition of exogenous arachidonic acid levels of $PGE_2$ in samples from both human osteosarcoma cells and COX-1 cells are approximately typically 0.1 to 2.0 ng/$10^6$ cells. In the presence of arachidonic acid, levels of $PGE_2$ in samples from these cell lines increased to approximately 5 to 10 fold in osteosarcoma cells and 50 to 100 fold in COX-1 cells. For purposes of this specification, cellular cyclooxygenase activity in each cell line is defined as the difference between $PGE_2$ levels in samples incubated in the absence or presence of arachidonic acid, with the level of detection being approximately 10 pg/sample. Inhibition of $PGE_2$ synthesis by test compounds is calculated between $PGE_2$ levels in samples incubated in the absence or presence of arachidonic acid.

Microsomal cyclooxygenase assay

Human osteosarcoma cells may be grown and maintained in culture as described above. $10^5$ to $10^7$ cells are plated in tissue culture plates such as available from NUNCLON and maintained in culture for 2 to 7 days. Cells may be washed with a suitable buffer such phosphate buffered saline; pH 7.2, (PBS). Cells are then removed from the plate, preferably by scraping into PBS. Samples may then be concentrated, such as by centrifuging at 400×g for 10 minutes at 4° C. Cell pellets or other concentrate are either stored at a suitable reduced temperature such as −80° C., or processed immediately. All further manipulations of the cells are preferably performed at 0°–4° C. Cell pellets or concentrates obtained from two tissue culture plates are resuspended in a standard protective buffer, such as Tris-Cl, pH 7.4, containing 10 mM EDTA, 1 mM phenyhnethylsulfonylfluoride, 2 μg/ml leupeptin, 2 μg/ml aprotinin, and 2 μg/ml soybean trypsin inhibitor and blended or homogenized, such as by sonication for three×5 seconds using a 4710 series ultrasonic homogenizer (COLE-PARMER) set at 75% duty cycle, power level 3. Enriched microsomal preparations are then prepared, such as by diferential centrifugation to yield an enriched microsomal preparation. In our prefered procedure, the first step consists of four sequential centrifugations of the cell homogenate at 10,000×g for 10 min at 4° C. After each centrifugation at 10,000×g the supernatant is retained and recentrifuged. Following the fourth centrifugation, the supernatant is centrifuged at 100,000×g for 60–90 min at 4° C. to pellet the microsomal fraction. The 100,000×g supernatant is discarded and the 100,000×g microsomal pellet is resuspended in a suitable buffer such as 0.1M Tris-Cl, pH 7.4, containing 10 mM EDTA and 0.25 mg/ml delipidized bovine serum albumin (COLLABORATIVE RESEARCH INCORPORATED). The resulting microsomal suspension is recentrifuged such as at 100,000×g for 90 min at 4° C. to recover the microsomes. Following this centrifugation the microsomal pellet is resuspended in a stabilizing buffer, such as 0.1 M Tris-Cl, pH 7.4, containing 10 mM EDTA at a protein concentration of approximately 2–5 mg/ml. Aliquots of osteosarcoma microsomal preparations may be stored at low temperature, such as at −80° C. and thawed prior to use.

As may be apreciated by those of skill in the art, Human or serum albumin or other albumin, may be used as an alternative to BSA. Applicants have found that while the procedure may be carried out using standard BSA or other albumin, delipidized BSA is preferred. In particular, by use of delipidized BSA, endogenous microsomal arachidonic acid can be reduced by a factor of 2 or greater, such that the arachidonic acid produced in the assay constituted at least 90% of the total. As may be appreciated by those of skill in the art, other lipid adsorbing or sequestering agents may also be used. For purposes of this specification microsomes from which the exogenous arachidonic acid has been reduced by a factor of approximately 2 or more shall be considered to be microsomes that are substantially free of exogenous arachidonic acid.

COX-1 cells are grown and maintained in culture as described above, washed in a suitable buffer, such as PBS, and cell pellets or concentrates stored, preferably at −80° C. Cell pellets or concentrates corresponding to approximately $10^9$ to $10^{10}$ cells were resuspended in a suitable buffer, such as 10 ml of 0.1M Tris-HCl, pH 7.4 and blended or homogenized, such as by sonication by 2×5 seconds and 1×10 seconds using a 4710 series ultrasonic homogenizer (COLE-PARMER) set at 75% duty cycle, power level 3. The cell homogenate is then concentrated and resuspended. In our preferred procedure the cell homogenate is centrifuged at 10,000×g for 10 minutes at 4° C. The supernatant fraction is then recentrifuged at 100,000×g for 2 hours at 4° C., and the resulting microsomal pellet resuspended in a suitable buffer, such as 0.1M Tris-HCl, 1 mM EDTA, pH 7.4 to a protein concentration of approximately 1 to 10 mg/ml. Aliquots of osteosarcoma microsomal preparations may be stored at reduced temperature and thawed prior to use.

Assay procedure

Microsomal preparations from Human osteosarcoma and COX-1 cells are diluted in buffer, such as 0.1M Tris-HCl, 10 mM EDTA, pH 7.4, (buffer A) to a protein concentration of 50 to 500 μg/ml. 10 to 50 μl of test compound or DMSO or other vehicle is added to 2 to 50 μl of buffer A. 50 to 500 μl of microsome suspension is then added, preferably followed by mixing and incubation for 5 minutes at room temperature. Typically, assays are perforated in either duplicate or triplicate. Peroxide-free arachidonic acid (CAYMAN) in buffer A is then added to a final concentration of 20 μM arachidonic acid, followed by incubation, preferably at room temperature for 10 to 60 minutes. Control samples contained ethanol or other vehicle instead of arachidonic acid. Following incubation, the reaction was terminated by addition of HCl or other mineral acid. Prior to analysis of $PGE_2$ levels, samples were neutralized. Levels of $PGE_2$ in samples may be quantitated as described for the whole cell cyclooxygenase assay.

Cyclooxygenase activity in the absence of test compounds was determined as the difference between $PGE_2$ levels in samples incubated in the presence of arachidonic acid or ethanol vehicle, and reported as ng of $PGE_2$/mg protein. Inhibition of $PGE_2$ synthesis by test compounds is calculated between $PGE_2$ levels in samples incubated in the absence or presence of arachidonic acid.

EXAMPLE 1

WHOLE CELL CYCLOOXYGENASE ASSAYS

Human osteosarcoma 143.98.2 cells were cultured in DULBECCOS MODIFIED EAGLES MEDIUM (SIGMA) containing 3.7 g/l $NaHCO_3$ (SIGMA), 100 μg/l gentamicin (GIBCO), 25 mM HEPES, pH 7.4 (SIGMA), 100 IU/ml penicillin (FLOW LABS), 100 μg/ml streptomycin (FLOW LABS), 2 mM glutamine (FLOW LABS) and 10% fetal bovine serum (GIBCO). Cells were maintained at 37° C., 6% $CO_2$ in 150 $cm^2$ tissue culture flasks (CORNING). For routine subculturing, media was removed from confluent cultures of cells, which were then incubated with 0.25% trypsin/0.1% EDTA (JRH BIOSCIENCES) and incubated at room temperature for approximately 5 minutes. The trypsin solution was then aspirated, and cells resuspended in fresh medium and dispensed at a ratio of 1:10 or 1:20 into new flasks.

U-937 cells (ATCC CRL 1593) were cultured in 89% RPMI-1640 (SIGMA), 10% fetal bovine serum (GIBCO), containing 50 IU/ml penicillin (Flow labs), 50 μg/ml streptomycin (FLOW LABS) and 2 g/l $NaHCO_3$ (SIGMA). Cells were maintained at a density of $0.1–2.0\times10^6$/ml in 1 liter spinner flasks (Corning) at 37° C., 6% $CO_2$. For routine subculturing, cells were diluted in fresh medium and transferred to fresh flasks.

ASSAY PROTOCOL

For cyclooxygenase assays, osteosarcoma 143.98.2 cells were cultured in 1 ml of media in 24-well multidishes (NUNCLON) until confluent. The number of cells per assay was determined from replicate plates prior to assays, using standard procedures. Immediately prior to cyclooxygenase assays, media was aspirated from cells, and the cells washed once with 2 ml of Hanks balanced salts solution (HBSS; SIGMA) prewarmed to 37° C. 1 ml of prewarmed HBSS was then added per well.

Immediately prior to cyclooxygenase assays, the appropriate number of U-937 cells were removed from spinner cultures and centrifuged at 300×g for 10 minutes. The supernatant was decanted and cells washed in 50 ml of HBSS prewarmed to 37° C. Cells were again pelleted at 300×g for 10 minutes and resuspended in prewarmed HBSS to a final cell density of approximately $1.5\times10^6$ cells/ml. 1 ml aliquots of cell suspension were transferred to 1.5 ml microcentrifuge tubes or 24-well multidishes (Nunclon).

Following washing and resuspension of osteosarcoma 143 and L-937 cells in 1 ml of HBSS, 1 μl of test compounds or DMSO vehicle were added, and samples gently mixed. All assays were performed in triplicate. Samples were then incubated for 5 minutes at 37° C., prior to the addition of 10 μl of peroxide-free arachidonic acid (CAYMAN) diluted to 1 μM in HBSS. Control samples contained ethanol vehicle instead of arachidonic acid. Samples were again gently mixed and incubated for a further 10 minutes at 37° C. For osteosarcoma cells, reactions were then stopped by the addition of 100 μl of 1N HCl, with mixing, or by the rapid removal of media directly from cell monolayers. For U-937 cells, reactions in multiwell dishes or microcentrifuge tubes were stopped by the addition of 10 μl of 1N HCl, with mixing. Samples assayed in 24-multidishes were then transferred to microcentrifuge tubes, and all samples were frozen on dry ice. Samples were stored at −20° C. prior to analysis of $PGE_2$ levels.

QUANTITATION OF $PGE_2$ CONCENTRATIONS

Osteosarcoma 143.98.2 and U-937 samples were thawed, and 100 μl of 1N NaOH added to samples to which 1N HCl had been added prior to freezing. Samples were then mixed by vortexing, and $PGE_2$ levels measured using a $PGE_2$ enzyme immunoassay (CAYMAN) according to the manufacturers instructions. The plating, washing and colour development steps of this procedure were automated using a BIOMEK 1000 (BECKMAN). Following the addition of ELLMANS reagent, color development was monitored at 415 nm using the Biorad model 3550 microplate reader with microplate manager/PC data analysis software. Levels of $PGE_2$ were calculated from the standard curve determined using BECKMAN IMMUNOFIT EIA/RIA analysis software.

RESULTS

In the absence of the addition of exogenous arachidonic acid, levels of $PGE_2$ in samples from both osteosarcoma 143 cells and U-937 cells were generally 2 ng/$10^6$ cells. In the presence of arachidonic acid, levels of $PGE_2$ in samples from these cell lines increased to approximately 5 to 10 fold in osteosarcoma cells and 50 to 100 fold in U-937 cells.

Table 1 show the effects of a series of non-steroidal antiinflammatory compounds on $PGE_2$ synthesis by human osteosarcoma 143 cells and U-937 cells in response to exogenous arachidonic acid.

TABLE 1

| SAMPLE | CONCENTRATION nM | osteosarcoma 143 PGE2 ng/$10^6$ cells | U-937 PGE2 |
|---|---|---|---|
| −AA | — | 1.8 | 0.15 |
| AA, no inhibitor | — | 8.6 | 17.7 |
| NS-389 | 100.0 | 0.8 | 18.9 |
| | 30.0 | 1.1 | 17.7 |
| | 10.0 | 3.0 | 20.4 |
| | 3.0 | 2.7 | 18.3 |
| | 1.0 | 3.2 | 17.7 |
| | 0.3 | 8.3 | 18.3 |
| Ibuprofen | 100,000 | 2.5 | 1.1 |
| | 10,000 | 5.7 | 5.5 |
| | 1,000 | 5.4 | 14.3 |
| | 300 | 10.8 | 15.8 |
| | 100 | 12.8 | 17.1 |
| | 10 | 12.5 | 16.4 |

EXAMPLE 2

MICROSOMAL CYCLOOXYGENASE ASSAY

Osteosarcoma 143.98.2 cells were grown and maintained in culture as described above. $3\times10^6$ cells were plated in 245×245×20 mm tissue culture plates (NUNCLON) and maintained in culture for 5 days. Cells were washed twice with 100 ml of phosphate buffered saline, pH 7.2, (PBS) and then scraped from the plate with a sterile rubber scraper into PBS. Samples were then centrifuged at 400×g for 10 minutes at 4° C. Cell pellets were either stored at −80° C. until use or processed immediately. All further manipulations of the cells were performed at 0°–4° C. Cell pellets obtained from two tissue culture plates were resuspended in 5 ml of 0.1M Tris-Cl, pH 7.4, containing 10 mM EDTA, 1 mM phenyhnethylsulfonylfluoride, 2 μg/ml leupeptin, 2 μg/ml aprotinin, and 2 μg/ml soybean trypsin inhibitor and sonicated for three×5 seconds using a 4710 series ultrasonic homogenizer (Cole-Parmer) set at 75% duty cycle, power level 3. The cell homogenates were then subjected to a differential centrifugation protocol to yield an enriched microsomal preparation. The first step consisted of four sequential centrifugations of the cell homogenate at 10,000×g for 10 min at 4° C. After each centrifugation at 10,000×g the supernatant was retained and recentrifuged. Following the fourth centrifugation, the supernatant was centrifuged at 100,000×g for 60–90 min at 4° C. to pellet the microsomal fraction. The 100,000×g supernatant was discarded and the 100,000×g microsomal pellet was resuspended in 8 mls of 0.1M Tris-Cl, pH 7.4, containing 10 mM EDTA and 0.25 mg/ml delipidized bovine serum albumin (COLLABORATIVE RESEARCH INCORPORATED). The resulting microsomal suspension was recentrifuged at 100,000×g for 90 min at 4° C. to recover the microsomes. Following this centrifugation the microsomal pellet was resuspended in 0.1M Tris-Cl, pH 7.4, containing 10 mM EDTA at a protein concentration of approximately 2–5 mg/ml. 500 μl aliquots of osteosarcoma microsomal preparations were stored at −80° C. and thawed on ice immediately prior to use.

U-937 cells were grown and maintained in culture as described above, washed in PBS, and cell pellets frozen at −80° C. Cell pellets corresponding to approximately $4\times10^9$ cells were resuspended in 10 ml of 0.1M Tris-HCl, pH 7.4 and sonicated for 2×5 seconds and 1×10 seconds using a 4710 series ultrasonic homogenizer (COLE-PARMER) set at 75% duty cycle, power level 3. The cell homogenate was then centrifuged at 10,000×g for 10 minutes at 4° C. The supernatant fraction was then recentrifuged at 100,000×g for 2 hours at 4° C., and the resulting microsomal pellet resuspended in 0.1M Tris-HCl, 1 mM EDTA, pH 7.4 to a protein concentration of approximately 4 mg/ml. 500 μl aliquots of osteosarcoma microsomal preparations were stored at −80° C. and thawed on ice immediately prior to use.

ASSAY PROTOCOL

Microsomal preparations from osteosarcoma 143 and U-937 cells were diluted in 0.1M Tris-HCl, 10 mM EDTA, pH 7.4, (buffer A) to a protein concentration of 100 μg/ml. All subsequent assay steps, including the dilution of stock solutions of test compounds, were automated using the BIOMEK 100 (BIORAD). 5 μl of test compound or DMSO vehicle was added with mixing, to 20 μl of buffer A in a 9-well minitube plate (BECKMAN). 200 μl of microsome suspension was then added, followed by mixing and incubation for 5 minutes at room temperature. Assays were performed in either duplicate or triplicate. 25 μl of peroxide-free arachidonic acid (CAYMAN) in buffer A is then added to a final concentration of 20 μM arachidonic acid, with mixing, followed by incubation at room temperature for 40 minutes. Control samples contained ethanol vehicle instead of arachidonic acid. Following the incubation period, the reaction was terminated by the addition of 25 μl of 1N HCl, with mixing. Prior to analysis of $PGE_2$ levels, samples were neutralized by the addition of 25 μl of 1N NaOH. Levels of $PGE_2$ in samples were quantitated by enzyme immunoassay (CAYMAN) as described for the whole cell cyclooxygenase assay.

TABLE II

MICROSOMAL ASSAY RESULTS - SET 1

| DRUG | 143.98.2 % Inhibition | U-937 % Inhibition |
|---|---|---|
| 100 nm DuP-697 | 92 | 6 |
| 3 uM DuP-697 | 93 | 48 |

TABLE II-continued

MICROSOMAL ASSAY RESULTS - SET 1

| DRUG | 143.98.2 % Inhibition | U-937 % Inhibition |
|---|---|---|
| 100 nM Flufenamic | 16 | 5 |
| 3 uM Flufenamic | 36 | 0 |
| 100 nM Flosulide | 13 | 0 |
| 3 uM Flosulide | 57 | 0 |
| 100 nM Zomipirac | 45 | 30 |
| 3 uM Zomipirac | 66 | 67 |
| 100 nM NS-398 | 45 | 0 |
| 3 uM NS-398 | 64 | 0 |
| 100 nM Diclofenac | 70 | 49 |
| 3 uM Diclofenac | 86 | 58 |
| 100 nM Sulindae sulfide | 19 | 0 |
| 3 uM Sulindae sulfide | 33 | 4 |
| 100 nM FK-3311 | 20 | 0 |
| 3 uM FK-3311 | 26 | 0 |
| 100 uM Fluribprofen | 55 | 57 |
| 3 uM Fluribprofen | 58 | 89 |

EXAMPLE 3

REVERSE TRANSCRIPTASE/POLYMERASE CHAIN REACTION

In order to confirm the type of cyclooxygenase mRNA present in osteosarcoma 143.98.2 cells, a reverse transcriptase polymerase chain reaction (RT-PCR) analytical technique was employed. Total RNA was prepared from osteosarcoma cells harvested 1–2 days after the cultures had reached confluence. The cell pellet was resuspended in 6 ml of 5M guanidine monothiocyanate containing 10 mM EDTA, 50 mM Tris-Cl, pH 7.4, and 8% (w/v) β-mercaptoethanol. The RNA was selectively precipitated by addition of 42 ml of 4M LiCl, incubation of the solution for 16 h at 4° C., followed by recovery of the RNA by centrifugation at 10,000×g for 90 min at 4° C. The RNA pellet which was obtained was resuspended in 10 mM Tris-HCl, pH 7.5, 1 mM EDTA, and 0.1% SDS at a concentration of 4 μg/ml and used directly for quantitation of COX-1 and COX-2 mRNAs by RT-PCR.

The quantitative RT-PCR technique employs pairs of synthetic oligonucleotides which will specifically amplify cDNA fragments from either COX-1, COX-2, or the control mRNA glyceraldehyde-3-phosphate-dehydrogenase (G3PDH). The synthetic oligonucleotides are described in Maier, Hla, and Maciag (J. Biol. Chem. 265: 10805–10808 (1990)); Hla and Maciag (J. Biol. Chem. 266: 24059–24063 (1991)); and Hla and Neilson (Proc. Natl. Acad. Sci., (USA) 89: 7384–7388 (1992)), and were synthesized according to the following sequences:

Human COX-1 specific oligonucleotides

5'-TGCCCAGCTCCTGGCCCGCCGCTT-3' SEQ. ID. NO:1:

5'-GTGCATCAACACAGGCGCCTCTTC-3' SEQ. ID. NO:2:

Human COX-2 specific oligonucleotides

5'-TTCAAATGAGATTGTGGGAAAATTGCT-3' SEQ. ID. NO:3:

5'-AGATCATCTCTGCCTGAGTATCTT-3' SEQ. ID. NO:4:

Human glyceraldehyde-3-phosphate dehydrogenase specific oligonucleotides

5'CCACCCATGGCAAATTCCATGGCA-3' SEQ. ID. NO:5:

5'-TCTAGACGGCAGGTCAGGTCCACC-3' SEQ. ID. NO:6:

The RT-PCR reactions were carried out using a RT-PCR kit from CETUS-PERKIN ELMER according to the manufacturers instructions. Briefly, 4 μg of osteosarcoma total RNA was reverse transcribed to cDNA using reverse transcriptase and random hexamers as primers for 10 min at 23° C., 10 min at 42° C., followed by an incubation at 99° C. for 5 min. The osteosarcoma cDNA sample was split into three equal aliquots which were amplified by PCR using 10 pmol of specific oligonucleotide pairs for either COX-1, COX-2, or G3PDH. The PCR cycling program was 94° C. for 1 min, 55° C. for 1 min, and 72° C. for 1 min. After the twentieth, twenty-fifth, and thirtieth cycle an aliquot was removed from the reaction mixture and stopped by the addition of 5 mM EDTA. Control reactions included RT-PCR reactions which contained no RNA and also reactions containing RNA but no reverse transcriptase.

Following RT-PCR the reactions were electrophoresed through a 1.2% agarose gel using a Tris-sodium acetate-EDTA buffer system at 110 volts. The positions of PCR-generated DNA fragments were determined by first staining the gel with ethidium bromide. The identity of the amplified DNA fragments as COX-1, COX-2, or G3PDH was confirmed by Southern blotting, using standard procedures. Nitrocellulose membranes were hybridized with radiolabelled COX-1, COX-2, or G3PDH-specific probes. Hybridization of the probes was detected by autoradiography and also be determining the bound radioactivity by cutting strips of the nitrocellulose which were then counted by liquid scintillation counting.

The RT-PCR/Southern hybridization experiment demonstrated that COX-2 mRNA is easily detected in osteosarcoma cell total RNA. No COX-1 cDNA fragment could be generated by PCR from osteosarcoma cell total RNA, although other mRNA species such as that for G3PDH are detected. These results demonstrate that at the sensitivity level of RT-PCR, osteosarcoma cells express COS-2 mRNA but not COX-1 mRNA.

Western blot of U-937 and 143.98.2 cell RNA

We have developed a rabbit polyclonal antipeptide antiserum (designated MF-169) to a thyroglobulin-conjugate of a peptide corresponding to amino acids 589–600, inclusive, of human cyclooxygenase-2. This amino acid sequence:

Asp-Asp-Ile-Asn-Pro-Thr-Val-Leu-Leu-Lys-Glu-Arg.

(also identified herein as SEQ. ID. NO:7:) has no similarity to any peptide sequence of human cyclooxygenase-1. At a dilution of 1:150, this antiserum detects by immunoblot a protein corresponding to the molecular weight of cyclooxygenase-2 in microsomal preparations from osteosarcoma 143 cells. The immunoblot procedure used for these studies has previously been described (Reid et at., J. Biol. Chem. 265: 19818–19823 (1990)). No band corresponding to the molecular weight of cyclooxygenase-2 is observed using a 1:150 dilution of pre-immune serum from the rabbit used to raise antiserum. Furthermore, a band corresponding to the molecular weight of cyclooxygenase-2 is observed by immunoblot in microsomal preparations of osteosarcoma 143 cells using a 1:150 dilution of a commercially available polyclonal antiserum against cyclooxygenase-2 (CAYMAN). This antiserum is reported to not cross-react with cyclooxygenase-1. These results clearly demonstrate that osteosarcoma 143 cells express cyclooxygenase-2. Furthermore, immunoblot analysis with these antisera and northern blot analysis using a COX-2-specific probe demonstrated that levels of cyclooxygenase-2 protein and the corresponding mRNA increase in osteosarcoma 143 cells as they grow past confluence. Within a 3-hour period, and in the presence of 1% serum, human recombinant IL 1-α (10 pg/ml; R and D systems Inc.) human recombinant IL 1-β (10 pg/ml; R and D systems Inc.), human EGF (15 ng/ml; CALBIOCHEM) and conditioned medium from cells grown beyond confluence also increased levels of $PGE_2$ synthesis of osteosarcoma 143 cells in response to arachidonic acid, relative to cells grown in the absence of these factors.

EXAMPLE 4

IDENTIFICATION BY NORTHERN BLOT ANALYSIS OF CELL LINES EXPRESSING EITHER COX-1 OR COX-2 EXCLUSIVELY

Northern blot analysis was used to determine that U-937 cells express only COX-1 mRNA whereas osteosarcoma 143.98.2 expresses only COX-2 mDNA. This was accomplished by first cloning human Cox-2 cDNA from total RNA of the human 143 osteosarcoma cell line. Total RNA was prepared from approximately $1\times10^8$ 143 osteosarcoma cells using 4M guanidinium isothiocyanate (Maniatis, et al. (1982) Molecular Cloning, Cold Spring Harbor). Oligonucleotide primers corresponding to the 5' and 3∝ ends of the published Cox-2 cDNA sequence (Hla and Neilson, (1992) Proc. Natl. Acad. Sci., USA 89, 7384–7388) were prepared and are shown below.

```
HCOX-1 5'CTGCGATGCTCGCCCGCGCCCTG3'  5'Primer

HCOX-2 5'CTTCTACAGTTCAGTCGAACOTTC3' 3'Primer
```

These primers (also identified hereinunder as SEQ. ID. NO:8 and SEQ. ID. NO:9: respectively) were used in a reverse transcriptase PCR reaction of 143 osteosarcoma total RNA. The reaction contained 1 ug of 143 osteosarcoma total RNA, which was first reverse transcribed using random hexamers and reverse transcriptase (Maniatis, et al. (1982) Molecular Cloning, Cold Spring Harbor). The products from this reaction were then amplified using the HCOX-1 and HCOX-2 primers described above and Taq polymerase (Saiki, et al. (1988) Science, 239, 487–488). The conditions used for the amplification were 94° C. for 30 sec, 55° C. for 30 sec and 72° C. for 2 min 15 sec for 30 cycles. The amplified products were run on a 1% low melt agarose gel and the 1.9 kb DNA fragment corresponding to the predicted size of human COX-2 cDNA was excised and recovered. An aliquot of the recovered COX-2 cDNA was reamplified as described above (no reverse transcriptase reaction), the amplified products were again run on a 1% low melt agarose gel and recovered.

By standard procedures as taught in Maniatis, et al. (1982) Molecular Cloning, Cold Spring Harbor, this 1.9 kb DNA fragment was cloned into the Eco RV site of pBluescript KS (obtained from STRATAGENE) and transformed into competent DH5α bacteria (obtained from BRL) and colonies selected on LB agar/ampicillian overnight. Three clones giving the correct Pst I and Hinc II restriction digestions for human COX-2 cDNA were sequenced completely and verified to be correct. This was the first indication that the human 143 osteosarcoma cell line expressed COX-2 mRNA.

Northern Analysis

Total RNA from various cell lines and tissues were prepared using the guanidinium isothiocyanate method as described above (Maniatis, et al. (1982) Molecular Cloning, Cold Spring Harbor). Poly A+ RNA was prepared using oligo dT cellulose spin columns (Maniatis, et al. (1982) Molecular Cloning, Cold Spring Harbor). The RNA, 10 μg of total or 5 μg of U937 Poly A+ were electrophoresed on 0.9% agarose 2.2M formaldehyde gels (Maniatis, et al. (1982) Molecular Cloning, Cold Spring Harbor). After electrophoreses the gel was washed 3 times for 10 minutes each with distilled water and then two times for 30 minutes each in 10XSSC (1XSSC=0.15M NaCl and 0.015 m sodium citrate). The RNA was transferred to nitrocellulose using capillary transfer (Maniatis, et al. (1982) Molecular Cloning, Cold Spring Harbor) overnight in 10XSSC. The next day the filter was baked in a vacuum oven at 80° C. for 1.5 hrs to fix the RNA onto the nitrocellulose. The filter was then equilibriated in pre-hybridization buffer (50% formamide, 6×SSC, 50 mM sodium phosphate buffer pH 6.5, 10×Denhardts solution, 0.2% SDS and 250 μg/ml of sheared and denatured salmon sperm DNA) for approximately 4 hours at 40° C. The COX-2 cDNA probe was prepared using $^{32}P$ dCTP and random hexamer priming with T7 DNA polymerase using a commercial kit (Pharmacia). Hybridization was carried out using the same buffer as for pre-hybridization plus $1–3\times10^6$ cpm/ml of denatured COX-2 cDNA probe at 40° C. overnight. The blots were washed two times in 1×SSC and 0.5% SDS at 50° C. for 30 minutes each, wrapped in saran wrap and exposed to Kodak XAR film with screen at −70° C. for 1–3 days. The same blots were stripped of COX-2 probe by putting them in boiling water and letting it cool to room temperature. The blot was re-exposed to film to ensure all hybridization signal was removed and then pre-hybridized and hybridized as described above using human COX-1 cDNA as probe. The human COX-1 cDNA was obtained from Dr. Colin Funk, Vanderbilt University, however the sequence is known in the art. See Funk, C. D., Funk, L. B., Kennedy, M. E., Pong, A. S., and Fitzgerald, G. A. (1991), FASEB J, 5 pp 2304–2312.

Using this Northern blot procedure applicants have established that the human 143 osteosarcoma cell line RNA hybridized only to the Cox-2 probe and not to the Cox-1 probe. The size of the hybridizing band obtained with the Cox-2 probe corresponded to the correct size of Cox-2 mRNA (approximately 4 kb) suggesting that 143 osteosarcoma cells only express Cox-2 mRNA and no Cox-1 mRNA. This has been confirmed by RT-PCR as described above. Similarly, the human cell line U937 Poly A+ RNA hybridized only to the Cox-1 probe and not to the Cox-2 probe. The hybridizing signal corresponded to the correct size for Cox-1 mRNA (approximately 2.8 kb) suggesting that U937 only express Cox-1 mRNA and not Cox-2. This was also confirmed by RT-PCR, since no product was obtained from U937 Poly A+ RNA when Cox-2 primers were used (see above).

EXAMPLE 5

Human Cyclooxygenase-2 cDNA and Assays for Evaluating Cyclooxygenase-2 Activity Examples demonstrating expression of the Cox-2 cDNA Comparison of the Cox-2 cDNA sequence obtained by RT-PCR of human osteosarcoma total RNA to the published sequence (Hla, Neilson 1992 Proc. Natl. Acad. Sci. USA, 89, 7384–7388), revealed a base change in the second position of codon 165. In the published sequence codon 165 is GGA, coding for the amino acid glycine, whereas in the osteosarcoma Cox-2 cDNA it is GAA coding for the amino acid glutamic acid.

To prove that osteosarcoma Cox-2 cDNA codes for glutamic acid at position 165 we repeated RT-PCR amplification of osteosarcoma Cox-2 mRNA; amplified, cloned and sequenced the region surrounding this base change from human genomic DNA; and used site directed mutagenesis to change Cox-$2_{glu165}$ to Cox-$2_{gly165}$ and compared there activities after transfection into COS-7 cells.

1. RT-PCR of Cox-2 mRNA from Human Osteosarcoma total RNA.

A 300 bp Cox-2 cDNA fragment that includes codon 165 was amplified by RT-PCR using human osteosarcoma 143 total RNA. Two primers:

```
Heox-13 5'CCTTCCTTCGAAATGCAATTA3' SEQ. ID. NO:12:

Heox-14 5'AAACTGATGCGTGAAGTGCTG3' SEQ. ID. NO:13:
```

were prepared that spanned this region and were used in the PCR reaction. Briefly, cDNA was prepared from 1 μg of osteosarcoma 143 total RNA, using random priming and reverse transcriptase (Maniatis et al., 1982, Molecular Cloning, Cold Spring Harbor). This cDNA was then used as a template for amplification using the Hcox-13 and Hcox-14 primers and Taq polymerase (Saki, et al. 1988, Science, 238, 487–488). The reaction conditions used were, 94° C. for 30s, 52° C. for 30s and 72° C. for 30s, for 30 cycles. After electrophoresis of the reaction on a 2% low melt agarose gel, the expected 300 bp amplified product was obtained, excised from the gel and recovered from the agarose by melting, phenol extraction and ethanol precipitation. The 300 bp fragment was ligated into the TAII cloning vector (Invitrogen) and transformed into E. Coli (INVαF) (Invitrogen). Colonies were obtained and 5 clones were picked at random which contained the 300 bp insert and sequenced. The sequence of codon 165 for all 5 clones was GAA (glutamic acid). Since the DNA sequence amplified was only 300 bp and the Taq polymerase has quite high fidelity for amplification of smaller fragments and its the second amplification reaction in which GAA was obtained for codon 165 confirms that Cox-2 mRNA from osteosarcoma has GAA for codon 165.

2. Amplification of Cox-2 codon 165 region from genomic DNA.

To confirm that the osteosarcoma Cox-2 sequence was not an artefact of the osteosarcoma cell line and that this sequence was present in normal cells, the DNA sequences containing codon 165 was amplified from human genomic DNA prepared from normal blood. The primers used for the amplification reaction were Hcox-13 and Hcox-14. The genomic organization of the human Cox-2 gene has not yet been determined. Using mouse Cox-2 gene organization as a model for the exon-intron positioning of the human Cox-2 gene would place primer Hcox-13 in exon 3 and Hcox-14 in exon 5. The size of the amplified product would be around 2000 bp based on the mouse Cox-2 gene organization. The PCR reaction contained 1 μg of human genomic DNA, Hcox-13 and Hcox-14 primers and Taq polymerase. The reaction conditions used were 94° C. for 30s, 52° C. for 30s and 72° C. for 45s, for 35 cycles. An aliquot of the reaction products was separated on a 1% low melt agarose gel. There were however a number of reaction products and to identify the correct fragment, the DNA was transferred to a nylon membrane by southern blotting and probed with a P-32 labelled human Cox-2 internal oligo.

```
Heox-17 5'GAGATTGTGGGAAAATTGCTT3' SEQ. ID. NO:14:
```

Hybridization was to a 1.4 kb DNA fragment which was recovered from the remainder of the PCR reaction by electrophoresis on a 0.8% low melt agarose gel as described above. This fragment was ligated into the TAII cloning vector (Invitrogen) and used to transform bacteria (as described above). A clone containing this insert was recovered and sequenced. The sequence at codon 165 was GAA (glutamic acid) and this sequence was from the human Cox-2 gene since the coding region was interrupted by introns. (The 3' splice site of intron 4 in human is the same as the mouse). This is very convincing evidence of the existance of a human Cox-2 having glutamic acid at position 165.

3. Cox-$2_{glu165}$ vs Cox-$2_{gly165}$ Activity in Transfected Cos-7 cells

To determine if Cox-$2_{glu165}$ has cyclooxygenase activity and to compare its activity to Cox-$2_{gly165}$, both cDNA sequences were cloned into the eukaryotic expression vector pcDNA-1 (Invitrogen) and transfected into COS-7 cells (see below). Activity was determined 48 h after transfection by incubating the cells with 20 μM arachidonic acid and measuring $PGE_2$ production by EIA (Cayman). The Cox-$2_{gly165}$ sequence was obtained by site directed mutagenesis of Cox-$2_{glu165}$. Briefly, single stranted KS+ plasmid (Stratagene) DNA containing the Cox-$2_{glu65}$ sequence cloned into the Eco RV site of the multiple cloning region was prepared by adding 1 ml of an overnight bacterial culture (XL-1 Blue (Stratagene) containing the COX-2 plasmid) to 100 ml of LB ampicillian (100 μg/ml) and grown at 37° C. for 1 hr. One ml of helper phage, M13K07, (Pharmacia) was then added and the culture incubated for an additional 7 hrs. The bacteria was pelleted by centrifugation at 10,000×g for 10 min, ¼ volume of 20% PEG, 3.5M ammonium acetate was added to the supernatant and the phage precipitated overnight at 4° C. The single stranded phage were recovered the next day be centrifugation at 17,000×g for 15 min, after an additional PEG precipitation the single stranded DNA was prepared from the phage by phenol and phenol:chorofonn extractions and ethanol precipitation. The single stranded DNA containing the Cox-$2_{glu165}$ sequence was used as template for site directed mutagenesis using the T7-GEN in vitro mutagenesis kit from U.S. Biochemical. The single stranded DNA (1.6 pmoles) was annealed to the phosphorylated oligo HCox-17 (16 pmoles), which changes codon 165 from GAA to GGA and the second strand synthesis carried out in the presence of 5-Methyl-dC plus the other standard deoxynucleoside triphosphates, T7 DNA polymerase and T4 DNA ligase. After synthesis the parental strand was nicked using the restriction endonuclease Msp 1 and then removed by exonuclease III digestion. The methylated mutated strand was rescued by transformation of E. coli mcAB-. Colonies were picked, sequenced and a number of clones were obtained that now had GGA for codon 165 instead of GAA. This Cox-$2_{gly165}$ sequence was released from the bluescript KS vector by an Eco RI-Hind III digestion, recovered and cloned into the eukaryotic expression vector pcDNA-1 (Invitrogen) which had also been digested with Eco RI-Hind HI. The Cox-$2_{glu165}$ sequence, was also cloned into the pcDNA-1 vector in the exact same manner. The only difference between the two plasmids was the single base change in codon 165.

The COX-2 pcDNA-1 plasmids were used to transfect Cos-7 cells using a modified calcium phospate procedure as described by Chen and Okyama (Chen, C. A. and Okyama, H. 1988. Biotechniques, 6, 632–638). Briefly, $5\times10^5$ Cos-7 cells were plated in a 10 cm culture dish containing 10 ml media. The following day one hour before transfection the media was changed. The plasmid DNA (1–30 μl) was mixed with 0.5 ml of 00.25M $CaCl_2$ and 0.5 ml of 2×BBS (50 mM N-, N-Bis(2-hydroxethyl)-2-amino-ethanesulfonic acid, 280 mM NaCl, 1.5 mM $Na_2HPO_4$) and incubated at room temperature for 20 min. The mixture was then added dropwise to the cells with swirling of the plate and incubated overnight (15–18 hrs) at 35° C. in a 3% $CO_2$ incubator. The next day the media was removed, the cells washed with PBS, 10 ml of fresh media added and the cells incubated for a further 48 hrs at 5% $CO_2$-37° C.

The cells were transfected with 2.5, 5 or 10 μg of Cox-$2_{glu165}$/pcDNA-1 or COX-$2_{gly165}$/pcDNA-1. Two plates were used for each DNA concentration and as a control the cells were transfected with pcDNA-1 plasmid. After 48 h the media was removed from the cells, the plates washed 3× with Hank's media and then 2 ml of Hank's media containing 20 μM arachidonic acid was added to the cells. After a 20 min incubation at 37° C. the media was removed from the plate and the amount of $PGE_2$ released into the media was measured by EIA. The $PGE_2$ EIA was performed using a commercially available kit (Caymen) following the manufacturers instructions. Shown in Table III is the amount of $PGE_2$ released into the media from Cos-7 cell transfected with pcDNA-1, Cos-7 transfected with Cox-$2_{glu165}$/pcDNA-1 and Cos-7 transfected with Cox-$2_{gly165}$/pcDNA-1. Depending on the amount of DNA transfected into the Cos-7 cells, Cox-$2_{glu165}$ is 1.3 to 2.3 times more active than Cox-$2_{gly165}$.

TABLE III

Level of $PGE_2$ pg/ml released from transfected Cos-7 cells

| Amount of Transfected DNA (μg) | 2.5 | 5.0 | 100.0 |
|---|---|---|---|
| | $PGE^2$ pg/ml | | |
| Cos-7 + Cox-$2_{glu\ 165}$/pcDNA1 | 1120 | 2090 | 4020 |
| Cos-7 + Cox-$2_{gly\ 165}$/pcDNA1 | 850 | 1280 | 1770 |

Cos-7 or Cos-7 + pcDNA1 (5 μg) < 3.9 pg/ml $PGE_2$

SEQUENCE LISTING (1) GENERAL INFORMATION:

(iii) NUMBER OF SEQUENCES: 14

(2) INFORMATION FOR SEQ ID NO: 1:

(i) SEQUENCE CHARACTERISTICS:
(A) LENGTH: 24 bases
(B) TYPE: nucleic acid
(C) STRANDEDNESS: single
(D) TOPOLOGY: linear (ii) MOLECULE TYPE: DNA (genomic)

(xi) SEQUENCE DESCRIPTION: SEQ ID NO: 1:

TGCCCAGCTC CTGGCCCGCC GCTT 24

(2) INFORMATION FOR SEQ ID NO: 2:

(i) SEQUENCE CHARACTERISTICS:
(A) LENGTH: 24 bases
(B) TYPE: nucleic acid
(C) STRANDEDNESS: single
(D) TOPOLOGY: linear (ii) MOLECULE TYPE: DNA (genomic)

(xi) SEQUENCE DESCRIPTION: SEQ ID NO: 2:

GTGCATCAAC ACAGGCGCCT CTTC 24

(2) INFORMATION FOR SEQ ID NO: 3:

(i) SEQUENCE CHARACTERISTICS:
(A) LENGTH: 27 bases
(B) TYPE: nucleic acid
(C) STRANDEDNESS: single
(D) TOPOLOGY: linear (ii) MOLECULE TYPE: DNA (genomic)

(xi) SEQUENCE DESCRIPTION: SEQ ID NO: 3:

TTCAAATGAG ATTGTGGGAA AATTGCT 27

(2) INFORMATION FOR SEQ ID NO: 4:

-continued (i) SEQUENCE CHARACTERISTICS:
(A) LENGTH: 24 bases
(B) TYPE: nucleic acid
(C) STRANDEDNESS: single
(D) TOPOLOGY: linear (ii) MOLECULE TYPE: DNA (genomic)

(xi) SEQUENCE DESCRIPTION: SEQ ID NO: 4:

AGATCATCTC TGCCTGAGTA TCTT 24

(2) INFORMATION FOR SEQ ID NO: 5:

(i) SEQUENCE CHARACTERISTICS:
(A) LENGTH: 24 bases
(B) TYPE: nucleic acid
(C) STRANDEDNESS: single
(D) TOPOLOGY: linear (ii) MOLECULE TYPE: DNA (genomic)

(xi) SEQUENCE DESCRIPTION: SEQ ID NO: 5:

CCACCCATGG CAAATTCCAT GGCA 24

(2) INFORMATION FOR SEQ ID NO: 6:

(i) SEQUENCE CHARACTERISTICS:
(A) LENGTH: 24 bases
(B) TYPE: nucleic acid
(C) STRANDEDNESS: single
(D) TOPOLOGY: linear (ii) MOLECULE TYPE: DNA (genomic)

(xi) SEQUENCE DESCRIPTION: SEQ ID NO: 6:

TCTAGACGGC AGGTCAGGTC CACC 24

(2) INFORMATION FOR SEQ ID NO: 7:

(i) SEQUENCE CHARACTERISTICS:
(A) LENGTH: 12 amino acids
(B) TYPE: amino acid
(C) STRANDEDNESS: single
(D) TOPOLOGY: linear (ii) MOLECULE TYPE: protein (xi) SEQUENCE DESCRIPTION: SEQ ID NO: 7:

Asp Asp Ile Asn Pro Thr Val Leu Leu Lys Glu Arg
1 5 10

(2) INFORMATION FOR SEQ ID NO: 8:

(i) SEQUENCE CHARACTERISTICS:
(A) LENGTH: 23 bases
(B) TYPE: nucleic acid
(C) STRANDEDNESS: single
(D) TOPOLOGY: linear (ii) MOLECULE TYPE: DNA (genomic)

(xi) SEQUENCE DESCRIPTION: SEQ ID NO: 8:

CTGCGATGCT CGCCCGCGCC CTG 23

(2) INFORMATION FOR SEQ ID NO: 9:

(i) SEQUENCE CHARACTERISTICS:
(A) LENGTH: 24 bases

-continued (B) TYPE: nucleic acid
(C) STRANDEDNESS: single
(D) TOPOLOGY: linear (ii) MOLECULE TYPE: DNA (genomic)

(xi) SEQUENCE DESCRIPTION: SEQ ID NO: 9:

CTTCTACAGT TCAGTCGAAC GTTC 24

(2) INFORMATION FOR SEQ ID NO: 10:

(i) SEQUENCE CHARACTERISTICS:
(A) LENGTH: 604 amino acids
(B) TYPE: amino acid
(C) STRANDEDNESS: single
(D) TOPOLOGY: linear (ii) MOLECULE TYPE: protein (xi) SEQUENCE DESCRIPTION: SEQ ID NO: 10:

```
Met Leu Ala Arg Ala Leu Leu Leu Cys Ala Val Leu Ala Leu Ser His
1               5                   10                  15

Thr Ala Asn Pro Cys Cys Ser His Pro Cys Gln Asn Arg Gly Val Cys
            20                  25                  30

Met Ser Val Gly Phe Asp Gln Tyr Lys Cys Asp Cys Thr Arg Thr Gly
        35                  40                  45

Phe Tyr Gly Glu Asn Cys Ser Thr Pro Glu Phe Leu Thr Arg Ile Lys
    50                  55                  60

Leu Phe Leu Lys Pro Thr Pro Asn Thr Val His Tyr Ile Leu Thr His
65                  70                  75                  80

Phe Lys Gly Phe Trp Asn Val Val Asn Asn Ile Pro Phe Leu Arg Asn
                85                  90                  95

Ala Ile Met Ser Tyr Val Leu Thr Ser Arg Ser His Leu Ile Asp Ser
            100                 105                 110

Pro Pro Thr Tyr Asn Ala Asp Tyr Gly Tyr Lys Ser Trp Glu Ala Phe
        115                 120                 125

Ser Asn Leu Ser Tyr Tyr Thr Arg Ala Leu Pro Pro Val Pro Asp Asp
    130                 135                 140

Cys Pro Thr Pro Leu Gly Val Lys Gly Lys Lys Gln Leu Pro Asp Ser
145                 150                 155                 160

Asn Glu Ile Val Glu Lys Leu Leu Leu Arg Arg Lys Phe Ile Pro Asp
                165                 170                 175

Pro Gln Gly Ser Asn Met Met Phe Ala Phe Phe Ala Gln His Phe Thr
            180                 185                 190

His Gln Phe Phe Lys Thr Asp His Lys Arg Gly Pro Ala Phe Thr Asn
        195                 200                 205

Gly Leu Gly His Gly Val Asp Leu Asn His Ile Tyr Gly Glu Thr Leu
    210                 215                 220

Ala Arg Gln Arg Lys Leu Arg Leu Phe Lys Asp Gly Lys Met Lys Tyr
225                 230                 235                 240

Gln Ile Ile Asp Gly Glu Met Tyr Pro Pro Thr Val Lys Asp Thr Gln
                245                 250                 255

Ala Glu Met Ile Tyr Pro Pro Gln Val Pro Glu His Leu Arg Phe Ala
            260                 265                 270

Val Gly Gln Glu Val Phe Gly Leu Val Pro Gly Leu Met Met Tyr Ala
        275                 280                 285

Thr Ile Trp Leu Arg Glu His Asn Arg Val Cys Asp Val Leu Lys Gln
    290                 295                 300
```

-continued

```
Glu His Pro Glu Trp Gly Asp Glu Gln Leu Phe Gln Thr Ser Arg Leu
305                 310                 315                 320

Ile Leu Ile Gly Glu Thr Ile Lys Ile Val Ile Glu Asp Tyr Val Gln
                325                 330                 335

His Leu Ser Gly Tyr His Phe Lys Leu Lys Phe Asp Pro Glu Leu Leu
            340                 345                 350

Phe Asn Lys Gln Phe Gln Tyr Gln Asn Arg Ile Ala Ala Glu Phe Asn
        355                 360                 365

Thr Leu Tyr His Trp His Pro Leu Leu Pro Asp Thr Phe Gln Ile His
    370                 375                 380

Asp Gln Lys Tyr Asn Tyr Gln Gln Phe Ile Tyr Asn Asn Ser Ile Leu
385                 390                 395                 400

Leu Glu His Gly Ile Thr Gln Phe Val Glu Ser Phe Thr Arg Gln Ile
                405                 410                 415

Ala Gly Arg Val Ala Gly Gly Arg Asn Val Pro Pro Ala Val Gln Lys
            420                 425                 430

Val Ser Gln Ala Ser Ile Asp Gln Ser Arg Gln Met Lys Tyr Gln Ser
        435                 440                 445

Phe Asn Glu Tyr Arg Lys Arg Phe Met Leu Lys Pro Tyr Glu Ser Phe
    450                 455                 460

Glu Glu Leu Thr Gly Glu Lys Glu Met Ser Ala Glu Leu Glu Ala Leu
465                 470                 475                 480

Tyr Gly Asp Ile Asp Ala Val Glu Leu Tyr Pro Ala Leu Leu Val Glu
                485                 490                 495

Lys Pro Arg Pro Asp Ala Ile Phe Gly Glu Thr Met Val Glu Val Gly
            500                 505                 510

Ala Pro Phe Ser Leu Lys Gly Leu Met Gly Asn Val Ile Cys Ser Pro
        515                 520                 525

Ala Tyr Trp Lys Pro Ser Thr Phe Gly Gly Glu Val Gly Phe Gln Ile
    530                 535                 540

Ile Asn Thr Ala Ser Ile Gln Ser Leu Ile Cys Asn Asn Val Lys Gly
545                 550                 555                 560

Cys Pro Phe Thr Ser Phe Ser Val Pro Asp Pro Glu Leu Ile Lys Thr
                565                 570                 575

Val Thr Ile Asn Ala Ser Ser Ser Arg Ser Gly Leu Asp Asp Ile Asn
            580                 585                 590

Pro Thr Val Leu Leu Lys Glu Arg Ser Thr Glu Leu
        595                 600
```

(2) INFORMATION FOR SEQ ID NO: 11:

(i) SEQUENCE CHARACTERISTICS:
(A) LENGTH: 3387 bases
(B) TYPE: nucleic acid
(C) STRANDEDNESS: single
(D) TOPOLOGY: linear (ii) MOLECULE TYPE: DNA (genomic)

(xi) SEQUENCE DESCRIPTION: SEQ ID NO: 11:

```
GTCCAGGAAC TCCTCAGCAG CGCCTCCTTC AGCTCCACAG CCAGACGCCC TCAGACAGCA     60

AAGCCTACCC CCGCGCCGCG CCCTGCCCGC CGCTGCGATG CTCGCCCGCG CCCTGCTGCT    120

GTGCGCGGTC CTGGCGCTCA GCCATACAGC AAATCCTTGC TGTTCCCACC CATGTCAAAA    180

CCGAGGTGTA TGTATGAGTG TGGGATTTGA CCAGTATAAG TGCGATTGTA CCCGGACAGG    240
```

-continued

```
ATTCTATGGA GAAAACTGCT CAACACCGGA ATTTTTGACA AGAATAAAAT TATTTCTGAA    300
ACCCACTCCA AACACAGTGC ACTACATACT TACCCACTTC AAGGGATTTT GGAACGTTGT    360
GAATAACATT CCCTTCCTTC GAAATGCAAT TATGAGTTAT GTGTTGACAT CCAGATCACA    420
TTTGATTGAC AGTCCACCAA CTTACAATGC TGACTATGGC TACAAAAGCT GGGAAGCCTT    480
CTCTAACCTC TCCTATTATA CTAGAGCCCT TCCTCCTGTG CCTGATGATT GCCCGACTCC    540
CTTGGGTGTC AAAGGTAAAA AGCAGCTTCC TGATTCAAAT GAGATTGTGG AAAAATTGCT    600
TCTAAGAAGA AAGTTCATCC CTGATCCCCA GGGCTCAAAC ATGATGTTTG CATTCTTTGC    660
CCAGCACTTC ACGCACCAGT TTTTCAAGAC AGATCATAAG CGAGGGCCAG CTTTCACCAA    720
CGGGCTGGGC CATGGGGTGG ACTTAAATCA TATTTACGGT GAAACTCTGG CTAGACAGCG    780
TAAACTGCGC CTTTTCAAGG ATGGAAAAAT GAAATATCAG ATAATTGATG GAGAGATGTA    840
TCCTCCCACA GTCAAAGATA CTCAGGCAGA GATGATCTAC CCTCCTCAAG TCCCTGAGCA    900
TCTACGGTTT GCTGTGGGGC AGGAGGTCTT TGGTCTGGTG CCTGGTCTGA TGATGTATGC    960
CACAATCTGG CTGCGGGAAC ACAACAGAGT ATGTGATGTG CTTAAACAGG AGCATCCTGA   1020
ATGGGGTGAT GAGCAGTTGT TCCAGACAAG CAGGCTAATA CTGATAGGAG AGACTATTAA   1080
GATTGTGATT GAAGATTATG TGCAACACTT GAGTGGCTAT CACTTCAAAC TGAAATTTGA   1140
CCCAGAACTA CTTTTCAACA AACAATTCCA GTACCAAAAT CGTATTGCTG CTGAATTTAA   1200
CACCCTCTAT CACTGGCATC CCCTTCTGCC TGACACCTTT CAAATTCATG ACCAGAAATA   1260
CAACTATCAA CAGTTTATCT ACAACAACTC TATATTGCTG GAACATGGAA TTACCCAGTT   1320
TGTTGAATCA TTCACCAGGC AAATTGCTGG CAGGGTTGCT GGTGGTAGGA ATGTTCCACC   1380
CGCAGTACAG AAAGTATCAC AGGCTTCCAT TGACCAGAGC AGGCAGATGA AATACCAGTC   1440
TTTTAATGAG TACCGCAAAC GCTTTATGCT GAAGCCCTAT GAATCATTTG AAGAACTTAC   1500
AGGAGAAAAG GAAATGTCTG CAGAGTTGGA AGCACTCTAT GGTGACATCG ATGCTGTGGA   1560
GCTGTATCCT GCCCTTCTGG TAGAAAAGCC TCGGCCAGAT GCCATCTTTG GTGAAACCAT   1620
GGTAGAAGTT GGAGCACCAT TCTCCTTGAA AGGACTTATG GGTAATGTTA TATGTTCTCC   1680
TGCCTACTGG AAGCCAAGCA CTTTTGGTGG AGAAGTGGGT TTTCAAATCA TCAACACTGC   1740
CTCAATTCAG TCTCTCATCT GCAATAACGT GAAGGGCTGT CCCTTTACTT CATTCAGTGT   1800
TCCAGATCCA GAGCTCATTA AAACAGTCAC CATCAATGCA AGTTCTTCCC GCTCCGGACT   1860
AGATGATATC AATCCCACAG TACTACTAAA AGAACGGTCG ACTGAACTGT AGAAGTCTAA   1920
TGATCATATT TATTTATTTA TATGAACCAT GTCTATTAAT TTAATTATTT AATAATATTT   1980
ATATTAAACT CCTTATGTTA CTTAACATCT TCTGTAACAG AAGTCAGTAC TCCTGTTGCG   2040
GAGAAAGGAG TCATACTTGT GAAGACTTTT ATGTCACTAC TCTAAAGATT TTGCTGTTGC   2100
TGTTAAGTTT GGAAAACAGT TTTTATTCTG TTTTATAAAC CAGAGAGAAA TGAGTTTTGA   2160
CGTCTTTTTA CTTGAATTTC AACTTATATT ATAAGGACGA AAGTAAAGAT GTTTGAATAC   2220
TTAAACACTA TCACAAGATG CCAAAATGCT GAAAGTTTTT ACACTGTCGA TGTTTCCAAT   2280
GCATCTTCCA TGATGCATTA GAAGTAACTA ATGTTTGAAA TTTTAAAGTA CTTTTGGGTA   2340
TTTTTCTGTC ATCAAACAAA ACAGGTATCA GTGCATTATT AAATGAATAT TTAAATTAGA   2400
CATTACCAGT AATTTCATGT CTACTTTTTA AAATCAGCAA TGAAACAATA ATTTGAAATT   2460
TCTAAATTCA TAGGGTAGAA TCACCTGTAA AAGCTTGTTT GATTTCTTAA AGTTATTAAA   2520
CTTGTACATA TACCAAAAAG AAGCTGTCTT GGATTTAAAT CTGTAAAATC AGATGAAATT   2580
TTACTACAAT TGCTTGTTAA AATATTTTAT AAGTGATGTT CCTTTTTCAC CAAGAGTATA   2640
```

-continued

```
AACCTTTTTA GTGTGACTGT TAAAACTTCC TTTTAAATCA AAATGCCAAA TTTATTAAGG   2700

TGGTGGAGCC ACTGCAGTGT TATCTCAAAA TAAGAATATC CTGTTGAGAT ATTCCAGAAT   2760

CTGTTTATAT GGCTGGTAAC ATGTAAAAAC CCCATAACCC CGCCAAAAGG GGTCCTACCC   2820

TTGAACATAA AGCAATAACC AAAGGAGAAA AGCCCAAATT ATTGGTTCCA AATTTAGGGT   2880

TTAAACTTTT TGAAGCAAAC TTTTTTTTAG CCTTGTGCAC TGCAGACCTG GTACTCAGAT   2940

TTTGCTATGA GGTTAATGAA GTACCAAGCT GTGCTTGAAT AACGATATGT TTTCTCAGAT   3000

TTTCTGTTGT ACAGTTTAAT TTAGCAGTCC ATATCACATT GCAAAAGTAG CAATGACCTC   3060

ATAAAATACC TCTTCAAAAT GCTTAAATTC ATTTCACACA TTAATTTTAT CTCAGTCTTG   3120

AAGCCAATTC AGTAGGTGCA TTGGAATCAA GCCTGGCTAC CTGCATGCTG TTCCTTTTCT   3180

TTTCTTCTTT TAGCCATTTT GCTAAGAGAC ACAGTCTTCT CAAACACTTC GTTTCTCCTA   3240

TTTTGTTTTA CTAGTTTTAA GATCAGAGTT CACTTTCTTT GGACTCTGCC TATATTTTCT   3300

TACCTGAACT TTTGCAAGTT TTCAGGTAAA CCTCAGCTCA GGACTGCTAT TTAGCTCCTC   3360

TTAAGAAGAT TAAAAAAAAA AAAAAAG                                       3387
```

```
(2) INFORMATION FOR SEQ ID NO: 12:

     (i) SEQUENCE CHARACTERISTICS:
          (A) LENGTH: 21 bases
          (B) TYPE: nucleic acid
          (C) STRANDEDNESS: single
          (D) TOPOLOGY: linear

    (ii) MOLECULE TYPE: DNA (genomic)

    (xi) SEQUENCE DESCRIPTION: SEQ ID NO: 12:

CCTTCCTTCG AAATGCAATT A                                              21
```

```
(2) INFORMATION FOR SEQ ID NO: 13:

     (i) SEQUENCE CHARACTERISTICS:
          (A) LENGTH: 21 bases
          (B) TYPE: nucleic acid
          (C) STRANDEDNESS: single
          (D) TOPOLOGY: linear

    (ii) MOLECULE TYPE: DNA (genomic)

    (xi) SEQUENCE DESCRIPTION: SEQ ID NO: 13:

AAACTGATGC GTGAAGTGCT G                                              21
```

```
(2) INFORMATION FOR SEQ ID NO: 14:

     (i) SEQUENCE CHARACTERISTICS:
          (A) LENGTH: 21 bases
          (B) TYPE: nucleic acid
          (C) STRANDEDNESS: single
          (D) TOPOLOGY: linear

    (ii) MOLECULE TYPE: DNA (genomic)

    (xi) SEQUENCE DESCRIPTION: SEQ ID NO: 14:

GAGATTGTGG GAAAATTGCT T                                              21
```

What is claimed is:

1. An assay for determining the cyclooxygenase-2 activity [of a sample] *of a composition comprising a human osteosarcoma cell preparation, a sample and arachidonic acid, the assay* comprising the steps of:

(a) *preparing the composition* adding (1) [a] *the* human osteosarcoma cell preparation, (2) [a] *the* sample, said sample comprising a putative cyclooxygenase-2 inhibitor, and (3) *the* arachidonic acid; and (b) determining the amount of prostaglandin $E_2$ produced in step (a).

2. An assay [for determining the cyclooxygenase-2 activity of a sample] according to claim 1 [comprising the steps of:

(a) adding (1) a human osteosarcoma cell preparation, (2) a sample, said sample comprising a putative cyclooxygenase-2 inhibitor, and (3) arachidonic acid; and (b) determining the amount of prostaglandin $E_2$ produced in step (a),]

wherein the cell preparation comprises $10^3$ to $10^9$ whole cells of osteosarcoma per cc, or 50 to 500 ug of osteosarcoma microsomes per ml of preparation; and 0.1 to 50 μl of arachidonic acid per ml of preparation.

3. An assay for determining the cyclooxygenase-2 activity of [a sample]*a composition comprising a human osteosarcoma cell preparation, a sample and arachidonic acid, the assay* comprising the steps of:

(a) *preparing the composition by* adding (1) [a] *the* human osteosarcoma cell preparation, (2) [a] *the* sample, said sample comprising a putative cyclooxygenase-2 inhibitor, and (3) *the* arachidonic acid; and (b) determining the amount of prostaglandin $E_2$ produced in step (a)

(c) [corrolating] *correlating* the amount of prostaglandin $E_2$ produced with cyclooxygenase-2 activity, wherein the osteosarcoma cell preparation consists essentially of osteosarcoma 143.98.2 microsomes.

4. An assay according to claim 3 wherein the osteosarcoma 143.98.2 microsomes are substantially free of endogenous arachidonic acid.

5. An assay according to claim 3 wherein the microsomes are contacted with an amount of delipidized serum protein effective to reduce the amount of endogenous arachidonic acid in the microsomes by a factor of at least approximately 2.

6. An assay for determining the cyclooxygenase-2 activity of [a sample] *a composition comprising a human osteosarcoma cell preparation, a sample and arachidonic acid, the assay* comprising the steps of:

(a) *preparing the composition by* adding (1) [a] *the* human osteosarcoma cell preparation, (2) [a] *the* sample, said sample comprising a putative cyclooxygenase-2 inhibitor, and (3) *the* arachidonic acid; and (b) determining the amount of prostaglandin $E_2$ produced in step (a), (c) [corrolating] *correlating* the amount of prostaglandin $E_2$ produced with cyclooxygenase-2 activity, wherein the human osteosarcoma cell preparation contains no recombinant vector.

7. An assay for determining the cyclooxygenase-2 activity of [a sample] *a composition comprising a human osteosarcoma cell preparation, a sample and arachidonic acid, the assay* comprising the steps of:

(a) *preparing the composition by* adding (1) [a] *the* human osteosarcoma cell preparation, (2) [a] *the* sample, said sample comprising a putative cyclooxygenase-2 inhibitor, and (3) *the* arachidonic acid; and (b) determining the amount of prostaglandin $E_2$ produced in step (a)

(c) [corrolating] *correlating* the amount of prostaglandin $E_2$ produced with cyclooxygenase-2 activity, wherein the osteosarcoma cell preparation consists essentially of whole cells of osteosarcoma 143.98.2.

[8. A composition comprising:

(a) an osteosarcoma cell preparation, having $10^3$ to $10^9$ osteosarcoma cells per cc of cell preparation or 50 to 500 μg of osteosarcoma microsomes; and (b) 0.1 to 50 μl of arachidonic acid per cc of cell preparation.]

[9. A composition according to claim 8 comprising $8\times10^4$ to $2\times10^6$ osteosarcoma 143.98.2 whole cells per cc of cell preparation or 100 to 400 μg of osteosarcoma 143.98.2 microsomes; and 10 to 20 μl of peroxide-free arachidonic acid per cc of cell preparation.]

[10. A composition according to claim 9 wherein the microsomes are substantially free of endogenous arachidonic acid.]

11. An assay for determining the cyclooxygenase-1 activity of [a sample] *a composition* comprising the steps of:

(a) *preparing the composition by* adding (1) a COX-1 cell preparation, *wherein the cell preparation consists essentially of whole cells of U-937 or U-937 microsomes,*

(2) a sample, said sample comprising a putative cyclooxygenase-1 inhibitor;

(3) arachidonic acid; and (b) determining the amount of prostaglandin $E_2$ produced in step (a)

[(c) corrolating the amount of prostaglandin $E_2$ produced with cyclooxygenase-2 activity].

12. An assay according to claim 11 wherein the COX-1 cell preparation consists essentially of whole cells of U-937.

13. An assay according to claim 11 wherein the COX-1 cell preparation consists essentially of U-937 microsomes.

14. An assay *according for claim 11* [for determining the cyclooxygenase-1 activity of a sample according to claim 10 comprising the steps of:

(a) adding (1) a COX-1 cell preparation, (2) a sample, said sample comprising a putative cyclooxygenase-1 inhibitor;

(3) arachidonic acid; and (b) determining the amount of prostaglandin $E_2$ produced in step (a),]

wherein the cell preparation comprises $10^5$ to $10^8$ whole cells of U-937 per cc, or 1 to 10 mg of U-937 microsomes per ml of preparation; and 0.1 to 50 μl of arachidonic acid per ml of preparation.

15. An assay according to claim 14 wherein the cell preparation comprises $8\times10^8$ to $1.5\times10^6$ whole cells of U-937 per cc, or 1 to 5 mg of U-937 microsomes per ml of preparation.

[16. Human Cyclooxygenase-2 cDNA which encodes protein of SEQ ID NO:10.]

[17. Human Cyclooxygenase-2 cDNA according to claim 15 comprising the coding region which is bases 97 to 1909 of FIG. 2 (SEQ ID NO:11:).]

[18. Human Cyclooxygenase-2 which is shown in FIG. 1 (SEQ ID NO:10:).]

19. *An isolated* [A transformed] host *cell* that expresses cyclooxygenase-2 [as shown in FIG. 1 (SEQ. ID. NO. 10:) comprising:] *wherein said host cell is transformed with*

[(a)] a mammalian or eukaryotic expression vector[; and (b)] *comprising* a sequence encoding [human] *said* cyclooxygenase-2 comprising bases 97 to 1909 [as shown in FIG. 2 (] *of* SEQ ID NO:11[)] or encodes [protein of FIG. 1 (] *the polypeptide* SEQ ID NO:10[)].

[20. A system according to claim 19 wherein the expression vector is a vacinia or baculovirus vector.]

[21. A system according to claim 19 wherein the cyclooxygenase-2 is expressed in COS-7 cells.]

*22. An isolated cyclooxygenase-2 cDNA comprising the coding region which is bases 97 to 1909 of SEO. ID. NO: 11.*

*23. A recombinant cyclooxygenase-2 consisting of SEO. ID. NO: 10.*

*24. An isolated cyclooxygenase-2 consisting of SEO. ID. NO: 10.*

*25. A purified cyclooxygenase-2 consisting of SEO. ID. NO: 10.*

*26. The transformed host cell according to claim 19 wherein the expression vector is a vacinia or baculovirus vector.*

*27. The transformed host cells according to claim 19 wherein said host cells are COS-7 cells.*

* * * * *